(12) United States Patent
Ohrbom et al.

(10) Patent No.: US 6,858,674 B2
(45) Date of Patent: Feb. 22, 2005

(54) CARBAMATE FUNCTIONAL MATERIALS, A METHOD OF MAKING SAID MATERIALS, AND CURABLE COATING COMPOSITIONS CONTAINING SAID MATERIALS

(75) Inventors: Walter H. Ohrbom, Hartland Township, MI (US); Craig S. Schang, Madison Heights, MI (US)

(73) Assignee: BASF Corporation, Southfield, MI (US)

( * ) Notice: Subject to any disclaimer, the term of this patent is extended or adjusted under 35 U.S.C. 154(b) by 188 days.

(21) Appl. No.: 10/285,594

(22) Filed: Oct. 31, 2002

(65) Prior Publication Data

US 2004/0087715 A1 May 6, 2004

(51) Int. Cl.$^7$ ............................................. C08F 8/32
(52) U.S. Cl. ........................ 525/157; 525/242; 525/481; 525/162; 525/452; 428/418; 428/447
(58) Field of Search ................................. 525/157, 242, 525/481, 162, 452; 428/418, 447

(56) References Cited

U.S. PATENT DOCUMENTS

| | | | |
|---|---|---|---|
| 2,979,514 A | 4/1961 | O'Brien ................ | 260/340.2 |
| 4,301,257 A | 11/1981 | Zengel et al. ........... | 525/329 |
| 4,710,542 A | 12/1987 | Forgione et al. ........ | 525/127 |
| 4,758,632 A | 7/1988 | Parekh et al. .......... | 525/383 |
| 4,939,213 A | 7/1990 | Jacobs, III et al. ..... | 525/329.9 |
| 5,084,541 A | 1/1992 | Jacobs, III et al. ..... | 528/45 |
| 5,288,865 A | 2/1994 | Gupta ................. | 544/200 |
| 5,356,669 A | 10/1994 | Rehfuss et al. ........ | 427/407.1 |
| 5,373,069 A | 12/1994 | Rehfuss et al. ........ | 525/456 |
| 5,474,811 A | 12/1995 | Rehfuss et al. ........ | 427/407.1 |
| 5,512,639 A | 4/1996 | Rehfuss et al. ........ | 525/456 |
| 5,552,497 A | 9/1996 | Taylor et al. .......... | 525/456 |
| 5,605,965 A | 2/1997 | Rehfuss et al. ........ | 525/100 |
| 5,719,237 A | * 2/1998 | Rehfuss et al. ........ | 525/419 |
| 5,907,024 A | * 5/1999 | Ohrbom et al. ........ | 528/75 |
| 5,945,499 A | 8/1999 | Ohrbom et al. ........ | 528/75 |
| 5,964,928 A | * 10/1999 | Tomlinson ............ | 106/14.21 |
| 5,976,615 A | * 11/1999 | Menovcik et al. ....... | 427/140 |
| 5,994,479 A | * 11/1999 | Green et al. .......... | 525/481 |
| 6,262,297 B1 | 7/2001 | Clements et al. ....... | 560/157 |
| 6,303,690 B1 | * 10/2001 | December et al. ...... | 525/163 |
| 6,362,285 B1 | 3/2002 | Ohrbom et al. ........ | 525/330.5 |
| 6,376,607 B1 | * 4/2002 | Ambrose et al. ....... | 525/101 |
| 6,391,968 B1 | * 5/2002 | Ohrbom et al. ........ | 525/162 |
| 6,580,001 B1 | 6/2003 | Bowman et al. ........ | 558/260 |
| 2002/0123545 A1 | 9/2002 | Yajking et al. ........ | 524/196 |
| 2002/0147279 A1 | * 10/2002 | Ohrbom et al. ........ | 525/157 |
| 2003/0100682 A1 | * 5/2003 | Ohrbom et al. ........ | 525/242 |
| 2003/0165688 A1 | * 9/2003 | Desai et al. .......... | 428/418 |

FOREIGN PATENT DOCUMENTS

| | | | |
|---|---|---|---|
| DE | 1063146 | * 7/1958 | |
| DE | 1593331 | * 10/1966 | |
| DE | 44 32 897 | 3/1996 | ........... C08L/61/20 |
| EP | 245 700 | 4/1987 | ......... C07D/251/54 |
| EP | 594 068 | 10/1993 | ......... C09D/201/02 |
| EP | 594 071 | 10/1993 | ......... C09D/201/02 |
| EP | 594 142 | 10/1993 | ........... C08L/57/12 |
| EP | 604 922 | 12/1993 | ......... C08K/5/3492 |
| EP | 850 986 | 12/1997 | ......... C08K/5/3492 |
| GB | 843331 | * 8/1957 | |
| GB | 1068650 | * 12/1965 | |
| WO | WO94/10211 | 5/1994 | ............. C08F/8/30 |
| WO | WO94/10212 | 5/1994 | ............. C08F/8/30 |
| WO | WO94/10213 | 5/1994 | ............. C08F/8/30 |
| WO | WO 01/56978 | 8/2001 | ........... C08K/5/205 |

OTHER PUBLICATIONS

International Search Report for PCT/US 03/30295, International Filing Date Sep. 24, 2003.
BASF Coating AG, Application No. USSN 10/182,528, filed Jul. 22, 2002, pp. 1–40.
Marvin L. Green, et al., entitled "Low VOC carbamate functional coatings compositions for automotive topcoats", Mar. 1–3, 2000, New Orleans, LA, USA.
W. Albert Noyes, Jr. The Journal of the American Chemical Society, vol. LXXIII, 1951.
English Abstract for DE44 32 897, Publication date Mar. 21, 1996, Constabel Martin et al.
American Cyanamid Co., B. Singh et al., entitled "Carbamylmethylated Melamines Novel Crosslinkers for the Coatings Industry", pp. 193–207, 1991, vol. 13.
Types of Paints and Coatings (Binders), entitled Urea, Benzogunanmine, and Melamine Resins for Coatings, pp. 80–86, 2nd Edition edited by Dieter Stope and Werner Freitag, 2001.
Shalom Sarel, et al. Organic Carbonates IV, entitled Factors Affecting Formation of Carbonates Homologous Cyclic, pp. 1873–1878, Dec. 1959.

(List continued on next page.)

*Primary Examiner*—David W. Wu
*Assistant Examiner*—Henry S. Hu

(57) ABSTRACT

The invention provides a primary carbamate functional material of the formula:

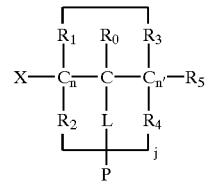

a method of making said materials and curable coating compositions comprising the primary carbamate functional material of the invention. The primary carbamate functional material comprises the reaction product of (1) at least one material P comprising one or more functional groups (i) which are reactive with a functional group Z but which are substantially nonreactive with a primary carbamate group X of monomeric reactive compound (2), and (2) a monomeric reactive compound comprising one or more structures of a particular formula.

62 Claims, No Drawings

OTHER PUBLICATIONS

J. Med. Chem., B. J. Ludwig, et al., entitled Carbamate derivatives related to, meprobamate, vol. 12, 1969, pp. 462–472.

English Abstract for JP 05138614, entitled "Persistent Preservative for Timber" Michihiko, et al., Date of Publication Aug. 6, 1993.*

English Abstract for JP 2002242075, entitled "Mildew-proof base fabric for night cover for refrigerator–freezer", date of publication Aug. 28, 2002.*

English Abstract for JP 63301251, entitled "Coating composition" Shuichi, et al., date of Publication Aug. 12, 1988.*

English Abstract for JP 05229973, entitled "Comprises adol condensation–dehydration of PrCHO in presence of aq. Alk. Soln. Catalyst, removal", et al., Date of Publication Sep. 7, 1993.*

Leon Palfray, et al., Compt. Rend. (1941) vol. 212, pp. 911 to 913 AN 1943:29287 Caplus.*

Database CA, online!, Chemical Abstract Service, Database Accession No. 128:2060676 CA, 1998, XP002265958.*

Walter H. Ohrbom, et al. USSN 10/285,634, filed Oct. 31, 2002, pp. 1–41 and abstract.*

Walter H. Ohrbom, et al. USSN 10/285, 600, filed Oct. 31, 2002, pp. 1–41 and abstract.*

Walter H. Ohrbom, et al. USSN 10/305,284, filed Nov. 26, 2002, pp. 1–49 and abstract.*

\* cited by examiner

CARBAMATE FUNCTIONAL MATERIALS, A METHOD OF MAKING SAID MATERIALS, AND CURABLE COATING COMPOSITIONS CONTAINING SAID MATERIALS

BACKGROUND OF THE INVENTION

Curable coating compositions such as thermoset coatings are widely used in the coatings art. They are often used for topcoats in the automotive and industrial coatings industry.

High-gloss and color-plus-clear composite coatings are particularly useful as topcoats where exceptional gloss, depth of color, distinctness of image, or special metallic effects are desired. The automotive industry has made extensive use of these coatings for automotive body panels. These coatings require an extremely high degree of clarity and a low degree of visual aberrations at the surface of the coating in order to achieve desired visual effects such as a high distinctness of image (DOI).

As a result, high-gloss and composite color-plus-clear coatings are susceptible to a phenomenon known as environmental etch. Environmental etch manifests itself as spots or marks on or in the finish of the coating that often cannot be rubbed out. It is often difficult to predict the degree of resistance to environmental etch that a high gloss or color-plus-clear composite coating will exhibit. Many coating compositions known for their durability and/or weatherability when used in exterior paints, such as high-solids enamels, do not provide the desired level of resistance to environmental etch when used in high gloss coatings and color-plus-clear composite coatings.

Many compositions have been proposed for use as the clearcoat of a color-plus-clear composite coating, such as polyurethanes, acid-epoxy systems and the like. However, many prior art systems suffer from disadvantages such as coatability problems, compatibility problems with the pigmented basecoat, solubility problems. Moreover, very few one-pack coating compositions have been found that provide satisfactory resistance to environmental etch, especially in the demanding environment of automotive coatings.

It has been found that carbamate functional polymers such as those described in U.S. Pat. No. 5,356,669 can be used to provide coating compositions which exhibit significantly improved environmental etch resistance. Carbamate functional polymers have been used to provide commercially advantageous coatings compositions, especially as clearcoats in composite color-plus-clear coatings.

Unfortunately, some carbamate functional compounds and/or polymers known in the prior art are vulnerable to instability and decomposition, especially with respect to the formation of cyclic carbonates and carbamates. This results in difficulties in manufacturing and storage.

It has also been difficult to make thermally stable hydroxy functional mono-carbamate functional compounds in an efficient and cost effective manner. In particular, what is desired is a commercially feasible method of making such compounds that utilizes cost effective starting compounds such as polyols and diols.

In addition, although coating compositions containing carbamate functional polymers generally provide the performance properties currently required by the automotive industry, continuous improvement is always desired. As a result, it would be advantageous to provide improvements in solids or % nonvolatile, flexibility, scratch & mar resistance, cold crack resistance, chip resistance and/or the like. At the same time, such improvements must be achieved without any decrease in environmental etch resistance or other commercially required performance property.

It would also be desirable to provide such a technology which would be applicable for use in a wide variety of coating compositions and applications, such as primers, basecoats, clearcoats, two-component systems, anti-chip coating compositions, water borne coatings, solvent borne coatings, coatings for flexible substrates, powder coatings, solventless powder-slurry coatings, solventless liquid coatings, and the like.

Finally, it would be advantageous to provide improved etch resistant coating compositions which have an increased % NV (nonvolatile) or decreased VOC (volatile organic content) at a sprayable viscosity.

The prior art has failed to address and rectify these issues.

The preparation of monocarbamate alcohols by the ammonolysis of cyclic carbonates prepared from substituted propanediols is disclosed in *Some Anticonvulsant Agents Derived from 1,3-Propanediols*, Ludwig, B. J. and Piech, E. C.; J. Am Chem. Soc. (1951) 73 5779–81. CAN 47:3228.

U.S. Pat. No. 5,719,237, Rehfuss et al., discloses the use of carbamate functional compounds (a) having a plurality of carbamate groups prepared by a transcarbamylation reaction wherein an alcohol or hydroxylalkyl carbamate is reacted with an alkyl carbamate. The '237 patent teaches that it is desirable to avoid the inclusion of hydroxyl groups in compound (a) as such hydroxyl groups lead to the formation of vulnerable ether bridges.

U.S. Pat. No. 5,907,024, Ohrbom et al., and U.S. Pat. No. 5,945,499 disclose the use of hydroxyalkyl carbamates of the general structure

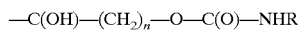

wherein n is an integer from 0 to 6 and R is H or an alkyl group of from 1 to 4 carbons.

U.S. Pat. No. 5,760,127, Bammel et al, and U.S. Pat. No. 6,262,297, Clements et al., disclose hydroxyalkylcarbamate compositions produced by the reaction of anhydrous ammonia or aqueous ammonium hydroxide with a six-membered cyclic carbonate. Bammel et al discloses that five-membered rings are preferred, not as a result of better performance, but as a result of their ease of synthesis and greater degree of commercial availability. Clements et al teaches that six-membered rings are preferred due to increased stability. However, the cost and commercial availability of the six-membered cyclic carbonates renders the process and resultant products to be less than cost effective. Also, depending on the location of any substituent groups on the starting cyclic carbonate, the process disclosed in Clements produces a reaction product which is a compound comprising a mixture of structures with varying reactivity and selectivity.

WO 0156978, Rink, et al discloses positionally isomeric diethyloctanediol dicarbamates and diethyloctanediols diallophanates. The dicarbamate and diallophanate species have no hydroxyl functionality and are made from position isomers of diethyloctane diols.

Despite these and other attempts by the prior art, the prior art has failed to provide a cost effective and efficient manner of making hydroxy functional mono-carbamate functional compounds from polyols and diols. Moreover, the prior art has particularly failed to provide such hydroxy functional mono-carbamate functional compounds that possess improved stability with respect to decomposition and the formation of undesirable cyclic carbonates and carbamates. As a result, the prior art has failed to provide carbamate functional polymers and/or oligomers that utilize such hydroxy functional mono-carbamate functional compounds as reactants and thus obtain the benefits thereof.

Accordingly, it is an object of the invention to provide carbamate functional polymers and/or oligomers which are made with compounds that possess improved stability with respect to the decomposition and the formation of undesirable cyclic carbonates and carbamates.

It is an another object of the invention to provide carbamate functional materials, including compounds, polymers or oligomers which are made from the polymerization reaction of mono-carbamate functional compounds containing hydroxy groups, halide groups or derivatives thereof with other compounds containing one or more groups reactive with hydroxy groups, halide groups, or derivatives thereof.

It is a further object of the invention to provide curable coating compositions containing carbamate functional materials which provide all of the advantages of prior art carbamate containing coating compositions, especially good environmental etch resistance, but further exhibit increased % NV (nonvolatile) or decreased VOC (volatile organic content) at a sprayable viscosity, and a desirable applied appearance.

It is also an object of the invention to provide curable coating compositions which provide all of the advantages of prior art carbamate containing coating compositions, especially good environmental etch resistance, but further exhibit improvement in one or more finished film performance parameters such as flexibility, scratch and mar resistance, and/or chip resistance.

It is another object of the invention to provide a technology for improving one or more of the following performance parameters, i.e., % nonvolatile solids, flexibility, scratch and mar resistance, and/or chip resistance, in a wide variety of coating compositions and applications, such as primers, basecoats, clearcoats, two-component systems, anti-chip coating compositions, water borne coatings, solvent borne coatings, coatings for flexible substrates, solventless coatings, powder coatings, and the like.

SUMMARY OF THE INVENTION

These and other objects of the invention have been met with a primary carbamate functional material of the formula:

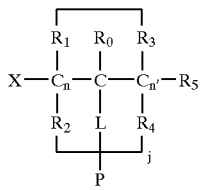

wherein X is a primary carbamate group, n is an integer of 2 or more, n' is an integer of 1 or more, $R_0$, $R_1$, $R_2$, $R_3$, $R_4$ and $R_5$ are independently H, an alkyl group, an aromatic group, or mixtures thereof, at least one $R_1$ or $R_2$ group is not hydrogen, L is a linking group, j is a number equal to 1 or greater, and P is a material selected from the group consisting of a compound, an oligomer, a polymer, and mixtures thereof. It is a requirement of the invention that all primary carbamate groups X in the above formula be attached to carbon atoms having a lower degree of substitution than a carbon atom to which linking group L is attached.

The invention also provides a method of the making the primary carbamate functional materials of the invention. The method requires the reaction of (1) at least one material P comprising one or more functional groups (i) which are reactive with a functional group Z but which are substantially nonreactive with a primary carbamate group X of monomeric reactive compound (2), and a monomeric reactive compound (2) comprising one or more structures of the formula:

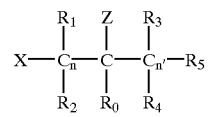

wherein X is a primary carbamate group, Z is a functional group reactive with at least one functional group of material (1) and is selected from the group consisting of hydroxy groups, halide groups, and derivatives thereof, n is an integer of 2 or more, n' is an integer of 1 or more, and $R_0$, $R_1$, $R_2$, $R_3$, $R_4$ and $R_5$ are independently H, an alkyl group, an aromatic group, or mixtures thereof, with the provisos that (i) at least one $R_1$ or $R_2$ group is not hydrogen, and (ii) in substantially all structures, primary carbamate group X is attached to a carbon atom having a lower degree of substitution than a carbon atom to which functional group Z is attached.

The method of the invention is advantageous because monomeric reactive compound (2) has improved stability over prior art compounds and can be used in harsher reaction conditions without undergoing appreciable decomposition.

The invention also provides curable coating compositions comprising one or more of the primary carbamate functional materials of the invention as a film-forming component or binder.

DETAILS OF THE PREFERRED EMBODIMENTS

The advantages of the instant invention derive from the use of a particular primary carbamate functional material of a particular formula. In a most preferred embodiment, the primary carbamate functional material will consist solely of this particular formula. The primary carbamate functional materials of the invention are of the formula:

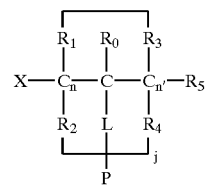

wherein X is a primary carbamate group, n is an integer of 2 or more, n' is an integer of 1 or more, $R_0$, $R_1$, $R_2$, $R_3$, $R_4$ and $R_5$ are independently H, an alkyl group, an aromatic group, or mixtures thereof, at least one $R_1$ or $R_2$ group is not hydrogen, L is a linking group, j is a number equal to 1 or greater, P is a material selected from the group consisting of a compound, an oligomer, a polymer, and mixtures thereof, and substantially all primary carbamate groups X are attached to carbon atoms having a lower degree of substitution than a carbon atom to which linking group L is attached The primary carbamate functional materials of the invention comprise the reaction product of (1) at least one material P and a monomeric reactive compound (2).

Monomeric reactive compound (2) comprises one or more structures of the formula:

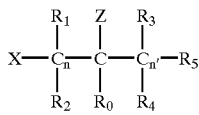

wherein X is a primary carbamate group, Z is a functional group reactive with at least one functional group of material P and is selected from the group consisting of hydroxy groups, halide groups, and derivatives thereof, n is an integer of 2 or more, n' is an integer of 1 or more, and $R_0$, $R_1$, $R_2$, $R_3$, $R_4$ and $R_5$ are independently H, an alkyl group, an aromatic group, or mixtures thereof. In addition, it is a necessary aspect of the invention that (i) at least one $R_1$ or $R_2$ group is not hydrogen, and (ii) in substantially all structures, primary carbamate group X is attached to a carbon atom having a lower degree of substitution than a carbon atom to which functional group Z is attached.

The term "structures" as used herein refers to isomers that satisfy the requirements of the instant invention. "Isomers" as used herein refers to structural and position isomers that have the same empirical chemical formula. Structures as used herein refer to those isomers that have the same empirical chemical formula but which satisfy the requirements of the instant formula. For the purposes of the instant invention, it will be appreciated that a single compound may comprise one or more than one structure. Illustrative examples of structural isomers are 2-ethyl-1,3-hexanediol and 2-propyl-1,3-pentanediol. Illustrative examples of position isomers are 2-ethyl-1,3-hexanediol and 2-ethyl-1,4-hexanediol. Illustrative examples of isomers which are both structural and position isomers are 2-ethyl-1,3-hexanediol and 2-propyl-1,4-pentanediol. However, it will be appreciated that only those isomers that satisfy the requirements of the instant invention may be structures of the reactive compound of the invention, i.e., they must (1) be of the formula:

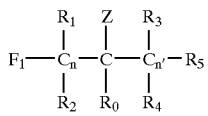

wherein X is a primary carbamate group, Z is either a hydroxy group, a halide group or a derivative thereof, n is an integer of 2 or more, n' is an integer of 1 or more, and $R_0$, $R_1$, $R_2$, $R_3$, $R_4$ and $R_5$ are independently H, an alkyl group, an aromatic group, or mixtures thereof, (2) at least one $R_1$ or $R_2$ group in this formula must not be hydrogen, and (3) most importantly, primary carbamate group X must be attached to a carbon atom having a lower degree of substitution than the carbon atom to which functional group Z is attached.

In general, the monomeric reactive compound (2) of the invention may comprise one or more structures that satisfy the above requirements. In a preferred embodiment, the monomeric reactive compound (2) will comprise at least two structures that are isomerically different as defined above but which each satisfy the above noted requirements of the invention. In a most preferred embodiment of the invention, the reactive compound of the invention will comprise at least four structures.

As noted above, it is an aspect of the invention that primary carbamate group X be attached to a carbon atom having a lower degree of substitution than the carbon atom to which functional group Z is attached. The term "lower degree of substitution" may be understood per the following statements. If X is a primary carbamate group attached to a primary carbon atom (i.e., X—CH$_2$—), Z will be functional group attached to either a secondary carbon atom (i.e., —Cn—CH(Z)—Cn'—) or a tertiary carbon atom (i.e., —Cn—CR$_0$(Z)—Cn'— wherein $R_0$ is not hydrogen and is an alkyl or aromatic containing group as further defined herein. If X is a primary carbamate group attached to a secondary carbon atom, i.e., (X—CHR—, wherein R is either $R_1$ or $R_2$ as defined above but is not hydrogen), Z must be a functional group attached to a tertiary carbon (i.e., —Cn—CR$_0$(Z)—Cn'— wherein $R_0$ is as defined above but is not hydrogen). It can be appreciated that because primary carbamate group X must be attached to a carbon atom having at least one fewer non-hydrogen substituent than that of the carbon atom to which functional group Z is attached, at least one of the substituents $R_1$ and $R_2$ must be hydrogen for the carbon to which X is attached.

As used herein, "primary carbamate group" refers to the functional group having the structure

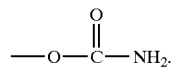

Thus, the primary carbamate group of the invention may be defined as a terminal or pendent carbamate group. In addition, it is an aspect of the method of the invention that the resultant reactive compounds will have one and only one primary carbamate group. That is, the reactive compounds produced by the instant method are limited to mono-carbamate functional compounds having at least one additional functional group that is either secondary or tertiary.

Monomeric reactive compounds (2) suitable for use herein will be substantially free of heteroatoms. "Heteroatoms" as used herein refers to atoms other than carbon or hydrogen. The phrase "substantially free of" as used herein means that the portion of monomeric reactive compound (2) which does not include the primary carbamate group X or the secondary or tertiary functional group Z will generally have no more than two atoms which are other than carbon or hydrogen, i.e., atoms such as N, O, Si, mixtures thereof, and the like. More preferably, that portion of monomeric reactive compound (2) that does not include primary carbamate group X or tertiary or secondary functional group Z will have no more than one atom that is other than carbon or hydrogen. In a most preferred embodiment, that portion of monomeric reactive compound (2) that does not include functional groups X and Z will have no heteroatoms, i.e., will consist solely of carbon and hydrogen atoms. Thus, in a most preferred aspect of the invention, the only heteroatoms in monomeric reactive compound (2) will be present in functional groups X and Z.

Functional group Z will be a hydroxyl group, a halide group or a functional derivative of a hydroxy group or a halide group. A "functional derivative of a hydroxy group or halide group" refers to a reactive functional group resulting from the reaction of a hydroxy or halide functional group Y, discussed below, with another functional group. A "reactive functional group" is a functional group that is reactive with functional group (i) of material P. Illustrative functional derivatives of hydroxy or halide groups include acid groups, epoxy groups, cyclic carbonate groups, silane groups, isocyanate groups, primary amine groups, secondary amine groups, silicon hydrides, alkenes, organometallic groups, mixtures thereof, and the like. Hydroxyl groups are most preferred for use as functional group Z.

It will be appreciated that functional group Z is not located on a primary carbon atom in the above formula.

Rather, functional group Z will be a secondary functional group when $R_0$ is H and will be a tertiary functional group when $R_0$ is an alkyl or aromatic containing group, i.e., an aliphatic group, a cycloaliphatic group, an aromatic group, or mixtures thereof. In a most preferred embodiment Z will be a secondary functional group and $R_0$ will be hydrogen.

In general, $R_0$, $R_1$, $R_2$, $R_3$, $R_4$ and $R_5$ may be H or an alkyl group, an aromatic group, or mixtures thereof. Illustrative alkyl groups are aliphatic groups and cycloaliphatic groups. Suitable alkyl and aromatic containing groups will generally have from one to sixteen carbon atoms and may be linear or branched. As used herein, the term "branched" refers to both lateral branches and forked branches. Lateral refers to a branch of two small chains at the end atom of a carbon chain. Forked refers to a branch of two small chains in the middle of a carbon chain. Any individual substituent may have both branching and forking therein. In addition, it is within the scope of the invention for two or more of the various R substituents to be connected with each other.

As noted above $R_0$ may be H or an alkyl or aromatic group containing substituent. In a most preferred embodiment $R_0$ will be H so that functional group Z is a secondary functional group. If $R_0$ is not hydrogen, suitable groups are those groups selected from the group of aliphatic, cycloaliphatic groups, aromatic groups and mixtures thereof. Preferred for use as $R_0$ are aliphatic and cycloaliphatic groups, with aliphatic groups being most preferred for use as $R_0$. Particularly suitable groups for use as $R_0$ are aliphatic groups and cycloaliphatic groups containing from one to sixteen carbon atoms, with aliphatic groups containing one to twelve carbon atoms being preferred if $R_0$ is an alkyl group and aliphatic groups containing one to eight carbon atoms being most preferred if $R_0$ is an alkyl group. Finally, it is within the scope of the invention that $R_0$ be an alkyl or aromatic group connected to any of the other $R_{1-5}$ substituents.

$R_1$, $R_2$, $R_3$, $R_4$ and $R_5$ may be H or a group as defined above for $R_0$.

However, it is an aspect of the invention that at least one $R_1$ or $R_2$ group must be selected from the group consisting of aliphatic groups, cycloaliphatic groups, aromatic groups, and mixtures thereof. That is, at least one of the $R_1$ and $R_2$ substituent groups must be other than hydrogen so long as primary carbamate group X is attached to a carbon atom having a lower degree of substitution than the carbon atom to which functional group Z is attached. Illustrative groups suitable for use as the $R_1$ or $R_2$ group that is not hydrogen are as defined above for $R_0$. Preferred for use as $R_1$ and $R_2$ are aliphatic and cycloaliphatic groups, with aliphatic groups being most preferred for use as $R_1$ or $R_2$ if they are not hydrogen. Particularly suitable non-hydrogen groups for use as $R_1$ and $R_2$ are aliphatic groups and cycloaliphatic groups containing from one to sixteen carbon atoms, with aliphatic groups containing from one to twelve carbon atoms being preferred if $R_1$ or $R_2$ is an alkyl group and aliphatic groups containing one to eight carbon atoms being most preferred if $R_1$ or $R_2$ is an alkyl group. Finally, it is within the scope of the invention that $R_1$ or $R_2$ be an alkyl or aromatic group connected to any of the other $R_{0, 3-5}$ substituents.

As noted above, because primary carbamate group X must be attached to a carbon atom having a lower degree of substitution than the carbon atom to which functional group Z is attached, at least one of the substituents $R_1$ and $R_2$ must be hydrogen for the carbon to which X is attached. This requirement is consistent with the requirement that at least one $R_1$ or $R_2$ group must be selected from the group consisting of aliphatic groups, cycloaliphatic groups, aromatic groups and mixtures thereof. When n is 2 and $R_0$ is not hydrogen, the at least one $R_1$ or $R_2$ group that is not hydrogen may be a substituent of the carbon immediately adjacent to the carbon attached to the primary carbamate group X. That is, the carbon to which the carbamate group is attached may have a primary or secondary degree of substitution. When n is greater than 2 and $R_0$ is not hydrogen, the at least one $R_1$ or $R_2$ group that is not hydrogen may be a substituent of the carbon to which the carbamate group is attached or to any of the carbons between the carbon attached to the primary carbamate group X and the carbon attached to the functional group Z, i.e., the $C_n$ carbons.

However, it is preferred that the at least one $R_1$ or $R_2$ group which is not hydrogen be attached to a carbon not directly attached to the carbamate group X. More preferably, the at least one $R_1$ or $R_2$ group that is not hydrogen will preferably be attached to a carbon atom located in closer proximity to functional group Z rather than functional X. When n is two, it will be appreciated that the at least one $R_1$ or $R_2$ group which is not hydrogen will most preferably be attached to a carbon atom located an equal distance between the carbons to which the functional groups X and Z are attached. When n is three or greater, the at least one $R_1$ or $R_2$ group which is not hydrogen will most preferably be attached to the carbon atom which is adjacent to the carbon atom to which the functional Z is attached or be in closer proximity thereto than to the carbon atom to which functional group X is attached.

It is another aspect of the invention that n be an integer of 2 or more so that functional groups X and Z are separated by at least three carbon atoms, including the carbon atoms to which are attached the functional groups X and Z. In one preferred embodiment of the invention, n will be an integer of from 2 to 12, more preferably from 2 to 8, and most preferably from 2 to 4. In another embodiment of the invention, n will be an integer of at least 3, more preferably from 3 to 12, and most preferably from 3 to 4.

In the monomeric reactive compound (2) used herein, n' must be an integer of 1 or more and may not be 0. In a preferred embodiment of the invention, n' will be an integer of from 1 to 16, more preferably from 1 to 12, and most preferably n' will be an integer of from 1 to 8.

$R_3$, $R_4$ and $R_5$ are selected from the group consisting of H, $C_1$–$C_{16}$ aliphatic groups, cycloaliphatic groups, aromatic groups, and mixtures thereof. In a preferred embodiment of the invention, $R_3$, $R_4$ and $R_5$ may be selected from the group consisting of H, aliphatic groups, cycloaliphatic groups, and mixtures thereof. In a most preferred embodiment, $R_3$, $R_4$ and $R_5$ will be selected from the group consisting of H, aliphatic groups, and mixtures thereof. In one embodiment according to the invention, $R_3$, $R_4$ and $R_5$ may be connected to $C_{n'}$, $R_0$, $R_1$ or $R_2$ to form a cyclic ring.

It is another aspect of the invention that in general, it is preferred that at least one of $R_3$, $R_4$ and $R_5$ will be a group other than hydrogen when n' is greater than 1. In a preferred embodiment, at least two of $R_3$, $R_4$ and $R_5$ will be other than hydrogen, i.e., $C_1$–$C_{16}$ aliphatic groups, cycloaliphatic groups, aromatic groups, and mixtures thereof, when n' is greater than 1. In a most preferred embodiment of the invention, when n' is greater than one, at least three of $R_3$, $R_4$ and $R_5$ will be selected from the group of $C_1$–$C_{16}$ aliphatic groups, cycloaliphatic groups, aromatic groups, and mixtures thereof.

In a most preferred embodiment, the monomeric reactive compounds (2) used herein will be made by a particular method. It is a particular advantage of the method of the invention used to make the monomeric reactive compound (2) that in the resulting reaction product substantially all of the structures therein possess a primary carbamate group X attached to a carbon atom having a lower degree of substitution than the carbon atom to which functional group Z is attached. It is a particular disadvantage of prior art processes that they fail to provide such a reaction product. Moreover, it is a most preferred aspect of the instantly disclosed method of making the primary carbamate functional materials of the invention, that it use only monomeric reactive compounds (2) made by this particular method.

As used herein, "substantially" refers to no more than 10% of the resulting mono-carbamate functional reaction product, i.e., the monomeric reactive compound (2), having a primary carbamate group attached to a carbon atom having a degree of substitution that is equal to or higher than that of the carbon atom to which the Z functional group is attached, preferably no more than 7%, and most preferably no more than 3%. It will be appreciated that amounts of unreacted starting materials are not part of this calculation.

The method of the invention requires that the monomeric reactive compounds (2) of the invention be made by reacting a compound (a) and a compound (b).

Compound (a) must have a functional group $F_i$ and a functional group $F_{ii}$ separated by at least three carbon atoms, wherein said functional groups $F_i$ and $F_{ii}$ are independently selected from the group consisting of functional groups convertible to primary carbamate groups, and functional group $F_i$ is attached to a carbon atom having a lower degree of substitution than a carbon atom to which functional group $F_{ii}$ is attached.

Functional groups $F_i$ and $F_{ii}$ are each independently selected from the group of functional groups convertible to primary carbamate groups. Preferred examples of functional groups $F_i$ and $F_{ii}$ convertible to primary carbamate groups are hydroxy groups and halide groups. Suitable halide groups include chloride, bromide, and iodide, with chloride being the most favored halide. Most preferably functional groups $F_i$ and $F_{ii}$ will be hydroxyl groups.

Suitable compounds (a) may include polyols, diols, polyhalides, and dihalides. However, the use of diols and dihalides as compound (a) is especially preferred as they are the most commercially available and economically feasible. Diols are most preferred for use as compound (a). Indeed, it is a particular benefit of the invention that it provides an economical and commercially feasible method of making thermally stable mono-carbamate compounds containing at least one functional group from compound (a) starting materials selected from the group consisting of dihalides and diols.

In a most preferred embodiment, compound (a) will be selected from the group of diols and dihalides of the following formula:

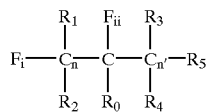

wherein $F_i$ and $F_{ii}$ are hydroxy or halide functional groups, n is an integer of 2 or more, n' is an integer of 1 or more, and $R_0$, $R_1$, $R_2$, $R_3$, $R_4$ and $R_5$ may individually be H or a group selected from the group of $C_1$–$C_{16}$ aliphatic groups, cycloaliphatic groups, aromatic groups, and mixtures thereof. However, it is an aspect of the invention that at least one $R_1$ or $R_2$ group be selected from the group consisting of $C_1$–$C_{16}$ aliphatic groups, cycloaliphatic groups, aromatic groups, and mixtures thereof. Functional group $F_i$ must be attached to a carbon atom having a lower degree of substitution than that of the carbon atom to which functional group $F_{ii}$ is attached.

Thus, it is an important aspect of the method of the invention that in compound (a), functional group $F_i$ will be attached to a carbon atom having a lower degree of substitution than the carbon atom to which functional group $F_{ii}$ is attached. For example, if $F_i$ is a primary functional group attached to a primary carbon atom (i.e., X—CH$_2$—), $F_{ii}$ will be functional group attached to either a secondary carbon atom (i.e., —C$_n$—CH(F$_{ii}$)—C$_{n'}$—) or a tertiary carbon atom (i.e., —C$_n$—CR$_0$(F$_{ii}$)—C$_{n'}$— wherein $R_0$ is not hydrogen and is as defined above). If $F_i$ is a primary functional group attached to a secondary carbon atom, i.e., (X—CHR—, wherein R is either $R_1$ or $R_2$ as defined above but is not hydrogen), $F_{ii}$ must be a functional group attached to a tertiary carbon, (i.e., —C$_n$—CR$_0$(F$_{ii}$)—C— wherein $R_0$ is not hydrogen and is as defined above). It can be appreciated that because functional group $F_i$ must be attached to a carbon atom having a lower degree of substitution than the carbon atom to which functional group $F_{ii}$ is attached, at least one of the substituents $R_1$ and $R_2$ on the carbon to which $F_i$ is attached must be hydrogen.

Most preferred compounds (a) will be substantially free of heteroatoms. "Heteroatoms" as used herein refers to atoms other than carbon or hydrogen. The phrase "substantially free of" as used herein means that the portion of compound (a) which does not include the functional groups $F_i$ and $F_{ii}$ will generally have no than two atoms which are other than carbon or hydrogen, i.e., atoms such as N, O, Si, mixtures thereof, and the like. More preferably, that portion of compound (a) that does not include functional groups $F_i$ and $F_{ii}$ will have no more than one atom that is other than carbon or hydrogen. In a most preferred embodiment, that portion of compound (a) that does not include functional groups $F_i$ and $F_{ii}$ will have no heteroatoms, i.e., will consist solely of carbon and hydrogen atoms. Thus, in a most preferred aspect of the invention, the only heteroatoms in compound (a) will be present in functional groups $F_i$ and $F_{ii}$.

It will be appreciated that functional group $F_{ii}$ is not located on a primary carbon atom in the above formula. Rather, functional group $F_{ii}$ will be a secondary functional group when $R_0$ is H and will be a tertiary functional group when $R_0$ is not hydrogen and is selected from the group of aliphatic groups, cycloaliphatic groups, aromatic groups, or mixtures thereof. In a most preferred embodiment $F_{ii}$ will be a secondary functional group and $R_0$ will be hydrogen.

In general, $R_0$, $R_1$, $R_2$, $R_3$, $R_4$ and $R_5$ may be H or an alkyl group, an aromatic group, or mixtures thereof. Illustrative alkyl groups are aliphatic groups and cycloaliphatic groups. Suitable alkyl and aromatic containing groups will generally have from one to sixteen carbon atoms and may be linear or branched. As used herein, the term "branched" refers to both lateral branches and forked branches. Lateral refers to a branch of two small chains at the end atom of a carbon chain. Forked refers to a branch of two small chains in the middle of a carbon chain. Any individual substituent may have both branching and forking therein. In addition, it is within the scope of the invention for two or more of the various R substituents to be connected with each other.

As noted above $R_0$ may be H or an alkyl or aromatic containing group or mixtures thereof. In a most preferred embodiment $R_0$ will be H so that functional group $F_{ii}$ is a secondary functional group. If $R_0$ is not hydrogen, suitable groups are those groups selected from the group of aliphatic groups, cycloaliphatic groups, aromatic groups and mixtures thereof. Preferred for use as $R_0$ are aliphatic and cycloaliphatic groups, with aliphatic groups being most preferred for use as $R_0$. Particularly suitable groups for use as $R_0$ are aliphatic groups and cycloaliphatic groups containing from one to sixteen carbon atoms, with aliphatic groups containing one to twelve carbon atoms being preferred if $R_0$ is an alkyl group and aliphatic groups containing one to eight carbon atoms being most preferred if $R_0$ is an alkyl group. Finally, it is within the scope of the invention that $R_0$ be an alkyl or aromatic group connected to any of the other $R_{1-5}$ substituents.

$R_1$, $R_2$, $R_3$, $R_4$ and $R_5$ may be H or a group as defined above for $R_0$.

However, it is an aspect of the invention that at least one $R_1$ or $R_2$ group must be selected from the group consisting of aliphatic groups, cycloaliphatic groups, and aromatic groups. That is, at least one of the $R_1$ and $R_2$ substituent groups must be other than hydrogen so long as functional group $F_i$ is attached to a carbon atom having a lower degree of substitution than the carbon atom to which functional group $F_{ii}$ is attached. Illustrative groups suitable for use as the $R_1$ or $R_2$ groups that are not hydrogen are those as defined above for $R_0$. Preferred for use as $R_1$ and $R_2$ are aliphatic and cycloaliphatic groups, with aliphatic groups being most preferred for use as $R_1$ or $R_2$ if they are not hydrogen. Particularly suitable non-hydrogen groups for use as $R_1$ and $R_2$ are aliphatic groups and cycloaliphatic groups containing from one to sixteen carbon atoms, with aliphatic groups containing from one to twelve carbon atoms being preferred if $R_1$ or $R_2$ is an alkyl group and aliphatic groups containing one to eight carbon atoms being most preferred if $R_1$ or $R_2$ is an alkyl group. Finally, it is within the scope of the invention that $R_1$ or $R_2$ be an alkyl or aromatic group connected to any of the other $R_{0, 3-5}$ substituents.

As noted above, because functional group $F_i$ must be attached to a carbon atom having a lower degree of substitution than the carbon atom to which functional group $F_{ii}$ is attached, at least one of the substituents $R_1$ and $R_2$ must be hydrogen for the carbon to which $F_i$ is attached. This requirement is consistent with the requirement that at least one $R_1$ or $R_2$ group must be selected from the group consisting of aliphatic groups, cycloaliphatic groups, aromatic groups and mixtures thereof. When n is 2 and $R_0$ is not hydrogen, the at least one $R_1$ or $R_2$ group that is not hydrogen may be a substituent of the carbon immediately adjacent to the carbon attached to the primary carbamate group X. That is, the carbon to which the carbamate group is attached may have a primary or secondary degree of substitution. When n is greater than 2 and $R_0$ is not hydrogen, the at least one $R_1$ or $R_2$ group that is not hydrogen may be a substituent of the carbon to which the carbamate group is attached or to any of the carbons between the carbon attached to the functional group $F_i$ and the carbon attached to the functional group $F_{ii}$, i.e., the $C_n$ carbons.

However, it is preferred that the at least one $R_1$ or $R_2$ group which is not hydrogen be attached to a carbon not directly attached to the functional group $F_i$. More preferably, the at least one $R_1$ or $R_2$ group that is not hydrogen will preferably be attached to a carbon atom located in closer proximity to functional group $F_{ii}$ rather than functional group $F_i$. When n is two, it will be appreciated that the at least one $R_1$ or $R_2$ group which is not hydrogen will most preferably be attached to a carbon atom located an equal distance between the carbons to which the functional groups $F_i$ and $F_{ii}$ are attached. When n is three or greater, the at least one $R_1$ or $R_2$ group which is not hydrogen will most preferably be attached to the carbon atom which is adjacent to the carbon atom to which the functional group $F_{ii}$ is attached or be in close proximity thereto than to the carbon atom to which the functional group $F_i$ is attached.

It is another aspect of the invention that n be an integer of 2 or more so that functional groups $F_i$ and $F_{ii}$ are separated by at least three carbon atoms, including the carbon atoms to which are attached the functional groups $F_i$ and $F_{ii}$. In one preferred embodiment of the invention, n will be an integer of from 2 to 12, more preferably from 2 to 8, and most preferably from 2 to 4. In another embodiment of the invention, n will be an integer of at least 3, more preferably from 3 to 12, and most preferably from 3 to 4.

In the most preferred compound (a) used in the method of the invention, n' must be an integer of 1 or more and may not be 0. In a preferred embodiment of the invention, n' will be an integer of from 1 to 16, more preferably from 1 to 12, and most preferably n' will be an integer of from 2 to 8.

$R_3$, $R_4$ and $R_5$ are selected from the group consisting of H, $C_1$–$C_{16}$ aliphatic groups, cycloaliphatic groups, aromatic groups, and mixtures thereof. In a preferred embodiment of the invention, $R_3$, $R_4$ and $R_5$ may be selected from the group consisting of H, aliphatic groups, cycloaliphatic groups, and mixtures thereof. In a most preferred embodiment, $R_3$, $R_4$ and $R_5$ will be selected from the group consisting of H, aliphatic groups, and mixtures thereof. In one embodiment according to the invention, $R_3$, $R_4$ and $R_5$ may be connected to $C_{n'}$, $R_0$, $R_1$ or $R_2$ to form a cyclic ring.

It is another aspect of the invention that in general, it is preferred that at least one of $R_3$, $R_4$ and $R_5$ will be a group other than hydrogen when n' is greater than 1. In a preferred embodiment, at least two of $R_3$, $R_4$ and $R_5$ will be other than hydrogen, i.e., $C_1$–$C_{16}$ aliphatic groups, cycloaliphatic groups, aromatic groups, and mixtures thereof, when n' is greater than 1. In a most preferred embodiment of the invention, when n' is greater than one, at least three of $R_3$, $R_4$ and $R_5$ will be selected from the group of $C_1$–$C_{16}$ aliphatic groups, cycloaliphatic groups, aromatic groups, and mixtures thereof.

Illustrative compounds (a) for use in a preferred embodiment of the method of the invention include 2-ethyl-1,3 hexanediol, 2-methyl-2,4-pentane diol, 2,2,4-trimethyl-1,3-pentanediol, 2,4-diethyl-1,5-octanediol, 1-hydroxymethyl cyclohexan-4-ol, and all those isomers thereof which satisfy the above requirements of the preferred formula for compound (a).

"Isomers" as used herein refers to structural and position isomers that have the same empirical chemical formula. An illustrative example of some structural isomers would be 2-ethyl-1,3-hexanediol and 2-propyl-1,3-pentanediol. An illustrative example of a position isomer would be 2-ethyl-1,3-hexanediol and 2-ethyl-1,4-hexanediol. An illustrative example of isomers which are both structural and position isomers would be 2-ethyl-1,3-hexanediol and 2-propyl-1,4-pentanediol. However, it will be appreciated that only those isomers that satisfy the requirements of the instant invention are suitable, i.e., they must (1) be of the formula:

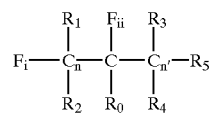

wherein $F_i$ and $F_{ii}$ are either hydroxy groups or halide groups, n is an integer of 2 or more, n' is an integer of 1 or more, and $R_0$, $R_1$, $R_2$, $R_3$, $R_4$ and $R_5$ are independently H, an alkyl group, an aromatic group, or mixtures thereof, (2)

at least one $R_1$ or $R_2$ group in this formula must not be hydrogen, and (3) most importantly, functional group $F_i$ must be attached to a carbon atom having a lower degree of substitution than the carbon atom to which functional group $F_{ii}$ is attached.

In one preferred embodiment, compound (a) will be selected from those members of the preferred formula for compound (a) that possess a particularly preferred isomeric distribution. 'Isomeric distribution' as used herein refers to the number of individual isomers that make up the material. A particularly preferred isomeric distribution is one in which compound (a) is a mixture of isomers having at least 4 or more individual isomers or structures. The resulting products made according to the invention from these materials have a greater tendency of being non-crystalline in nature. This is of advantage for obtaining low VOC coatings.

However, it will be appreciated that even compounds (a) consisting of one structure or isomer will provide acceptable levels of performance with respect to low VOC coatings. While not wishing to be bound to a particular theory, it is believed that this is attributable to the low degree of symmetry found in particular compounds (a) and thus in the final monomeric reactive compounds (2) of the invention.

It will be appreciated that the selection of compound (b) is somewhat dependent upon the selection of functional groups $F_i$ and $F_{ii}$ of compound (a). In general, if functional group ($F_i$) is a hydroxyl group, it will be converted into a primary carbamate by reaction with a compound (b) selected from the group consisting of alkyl carbamates, cycloalkyl carbamates, ether carbamates, beta hydroxy alkyl carbamates, aryl carbamates, cyanic acid produced, for example, by the decomposition of urea, and phosgene followed by reaction with ammonia. If functional group ($F_i$) is a halide group, it may be converted into a primary carbamate group by reaction with a metal carbamate such as silver carbamate as discussed in P. Adams & F. Baron, "Esters of Carbamic Acid", Chemical Review, v. 65, 1965. In a preferred embodiment, compound (b) will be selected from the group of alkyl carbamates, cycloalkyl carbamates, ether carbamates and aryl carbamates, and mixtures thereof, with alkyl carbamates being most preferred as compound (b).

Illustrative alkyl carbamates, cycloalkyl carbamates, and aryl carbamates include methyl carbamate, propyl carbamate, n-butyl carbamate, cyclohexyl carbamate, t-butyl carbamate, isopropyl carbamate, and phenyl carbamate. An example of a hydroxy alkyl carbamate is hydroxy ethyl carbamate. An example of an ether carbamate is 2-methoxyethyl carbamate. It will be appreciated that when (b) is selected from these compounds, reaction with suitable compounds (a) results in alcohols, phenols, ether alcohols and related materials as by-products. Examples of most preferred alkyl carbamates for use as compound (b) include methyl carbamate, isopropyl carbamate and n-butyl carbamate.

Compound (a) and compound (b) are reacted under conditions intended to minimize the formation of functional group ($F_{ii}$) to a carbamate group. In general, compounds (a) and (b) will reacted under conditions such that no more than 10% of the functional group (ii) is converted to a carbamate group, based on the starting amount of compound (a). More preferably, compounds (a) and (b) will be reacted under conditions such that no more than 5% of functional group ($F_{ii}$) is converted to a carbamate group, and most preferably no more than 4% of functional group ($F_{ii}$) will be converted to a carbamate group, all based on the starting amount of compound (a).

Thus, the formation of dicarbamate species is highly disfavored in the method of the invention. One technique to disfavor the formation of the dicarbamate is to use a deficit amount of compound (b), that is, the equivalent of the functional groups of compound (b) is less than the equivalent amount of functional group $F_i$ based on the starting amount of compound (a). In this case, the equivalent amount of compound (b) used in relationship to functional group $F_i$ can range from 0.99 to 1 to 0.25 to 1. An alternative technique that can be used to disfavor the formation of the dicarbamate when one or more than one equivalent of compound (b) are used in comparison to functional group $F_i$ on compound (a) is to stop the reaction before all of functional $F_i$ is converted to a primary carbamate. This second technique works best for reaction conditions that have a high degree of selectivity such as transcarbamation reactions. In comparison, this technique would be disfavored in a more nonselective reaction such as that between a hydroxy group and cyanic acid.

While not wishing to be bound to a particular theory, it is believed that the effectiveness of these two approaches can be increased by increasing the relative degree of steric hindrance surrounding functional groups $F_i$ and $F_{ii}$ on compound (a). That is, in general, dicarbamate formation can be diminished if the degree of steric hindrance surrounding functional group $F_{ii}$ is greater than the degree of steric hindrance on functional group $F_i$. This relationship is believed to hold true regardless of the method of reaction selected.

If not all of functional group $F_i$ has been transformed into a primary carbamate, the excess amount of unreacted starting material (a) can be removed by known techniques, such as vacuum distillation, extraction or filtration or may be left in as discussed below.

In some cases, the presence of unreacted (a) in the monomeric reactive compound (2) may be desirable in the reaction processes used to make the primary carbamate functional materials of the invention. If left in the reaction processes used to make the primary carbamate functional materials of the invention, the presence of unreacted (a) can act as a solvent, a reactive diluent or both. Alternatively, any excess amount of unreacted (a) may first be removed as described above.

It will be appreciated that the reaction of compounds (a) and (b) produces a reactive compound of the formula:

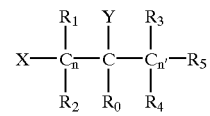

wherein X is a primary carbamate group, Y is a hydroxy or halide group, n is an integer of 2 or more, n' is an integer of 1 or more, and $R_0$, $R_1$, $R_2$, $R_3$, $R_4$ and $R_5$ may be independently H or a group selected from aliphatic groups, cycloaliphatic groups, aromatic groups and mixtures thereof, with the provisos that (i) at least one of the $R_1$ and $R_2$ groups is not hydrogen, and (ii) primary carbamate group X is attached to a carbon atom having a lower degree of substitution than a carbon atom to which functional group Y is attached.

While this reactive compound containing functional group Y can be used directly as the monomeric reactive compound (2) of the invention, it can also be used as a precursor to form monomeric reactive compound (2) containing functional group Z. While both functional group Z and functional group Y may be either a hydroxy group or a halide group, functional group Z may also be selected from the group consisting of functional derivatives of hydroxy groups and halide groups. As discussed above, functional derivatives of hydroxy groups and halide groups are those reactive functional groups resulting from single or multistep reactions of a hydroxy or halide group with one or more functional groups. Illustrative derivatives of hydroxy or halide groups include acid groups, epoxy groups, cyclic carbonate groups, silane groups, isocyanate groups, amine groups especially primary and secondary amines, silicon hydrides, alkenes, organometallics, mixtures thereof, and the like.

Examples of suitable functional group reactants used to obtain particular functional derivatives of either hydroxy groups or halide groups are illustrated in the following table. It should be noted that the recitation of more than one reactant refers to a multistep reaction process wherein the first functional derivative of Y is subsequently reacted with the next reactant to make the next or desired functional derivative of Y. It is within the scope of this invention for suitable functional groups used in the conversion of Y to Z to be part of compounds suitable for use as material P disclosed herein.

| Functional Group Y | Reactant(s) | Functional Derivative of Y |
|---|---|---|
| OH | diisocyanate | isocyanate |
| OH | cyclic anhydride | acid |
| OH | epoxy | alcohol |
| OH | methacrylic acid | alkene |
| OH | methacrylic anhydride | alkene |
| OH | silicon hydride | silane |
| halide (Cl, Br, F, or I) | ammonia | primary amine |
| halide (Cl, Br, F, or I) | primary amine | secondary amine |
| halide (Cl, Br, F, or I) | alkali and alkali earths metals (Mg, Na, Li) | organometallics |
| halide (Cl, Br, F, or I) | alkali earth metal/allyl iodide/peroxide/carbon dioxide | organometallic/alkene/ epoxy/cyclic carbonate |
| halide (Cl, Br, F, or I) | ammonia/phosgene | primary amine/isocyanate |
| halide (Cl, Br, F, or I) | alkali and alkali earth/ketone | organometallic/hydroxy |

It will be appreciated that a hydroxy group or halide group may be an original functional group Y or may be a derivative resulting from one or more derivative reactions. For example, a halide group Y may be converted into a hydroxy group by an initial reaction with an alkali or alkali earth to produce an organometallic followed by subsequent reaction of the organometallic with a ketone to provide a hydroxy group. However, those of skill in the art will appreciate that a 'derivative' hydroxy group will be different in structure than an 'original' hydroxy group. In particular, the 'derivative' hydroxy group will now contain the reaction product residue from the derivatization reaction processes, i.e., in this case, a ketone backbone will remain. Such reaction product residues may or may not contain additional functionality suitable for subsequent conversions or reactions. If such additional reactive functional groups are present in the reaction product residue, they are considered to be within the definition of functional derivative groups of hydroxy or halide groups.

In general, it is preferred that original hydroxy groups or halide groups Y be used as functional group Z if Z is hydroxy or halide.

It will be appreciated that the foregoing examples are illustrative only and that many other variations in reactants and reaction processes can be used to obtain desirable functional derivatives of halide or hydroxy groups, especially with regards to multistep reaction processes. Moreover, the use of various catalysts, work-up reagents, initiators, and reaction conditions in the foregoing reaction processes are held to be within the knowledge and experience of those of ordinary skill in the art.

The material P that is reacted with monomeric reactive compound (2) is selected from the group consisting of compounds, oligomers, polymers, and mixtures thereof. The material P must comprise one or more functional groups (i) which are reactive with a functional group Z as defined above but which are substantially nonreactive with a primary carbamate group X of monomeric reactive compound (2).

Material P is selected from the group consisting of compounds, oligomers, polymers, and mixtures thereof. In general, material P is a hydrocarbon-based material that may or may not contain heteroatoms in those portions of material P not including functional group (i) and any optional functional groups. "Heteroatoms" as used herein refers to atoms other than carbon or hydrogen. Preferred heteroatoms are O, N, Si, and mixtures thereof. Material P may be aliphatic, cycloaliphatic, aromatic, unsaturated, saturated, and mixtures thereof. In general, the material P may have a number average molecular weight of from 68 to 1,000,000 Daltons.

For the purposes of the instant invention, the term "oligomer" refers to materials having from two to nine repeating units or mixtures of repeating units. In general, suitable oligomers for use in the instant invention will have number average molecular weights in the range of from 200 to 1499 Daltons.

"Polymer" as used herein refers to materials having at least ten repeating units, more preferably greater than 10 repeating units. In general, polymers suitable for use as material P will have a number average molecular weight in the range of from 1500 to 1,000,000 Daltons, preferably between 1500 and 50,000 Daltons, most preferably between 1500 and 15,000 Daltons.

"Compounds" as used herein refers to materials that do not contain two or more of the same repeating units. In general, compounds will have number average molecular weights in the range of from 68 to 2000.

The term "repeating units" as defined as herein refers to groups of atoms that are the reaction product result or residue of the reaction of two or more monomers. Such repeating units will generally have an individual number average molecular weight in the range of from 28 to 750 Daltons.

While material P may be a compound, an oligomer, a polymer or a mixture thereof, material P will preferably be a polymer and/or oligomer, and most preferably an oligomer.

The material P must comprise one or more functional groups (i) which are reactive with a functional group Z but which are substantially nonreactive with a primary carbamate group X of monomeric reactive compound (2).

"Substantially nonreactive" as used herein refers to a reactive functional group (i) which does not react with the primary carbamate group under the conditions in which material P is reacted with monomeric reactive compound (2). In general, no more than 7% of primary carbamate group X will be reacted, preferably no more than 5%, and most preferably no more than 3% of primary carbamate group X will be reacted, based on the starting amount of monomeric reactive compound (2).

In general, functional groups (i) are those functional groups that are reactive with a functional group Z as defined above. Suitable functional groups (i) will thus encompass all functional groups reactive with either hydroxy groups, halide groups or any derivatives thereof as defined above. Illustrative functional groups (i) include hydroxy groups, cyclic anhydrides, anhydride groups, carboxylic acid groups, epoxy groups, cyclic carbonate groups, organometallic materials such as sodium or lithium alkanes, metal alkoxides, silane groups, isocyanate groups, primary amine groups, secondary amine groups, silicon hydrides, alkenes, mixtures thereof, and the like. Preferred functional groups (i) are carboxylic acid groups, alkenes, isocyanates, cyclic anhydrides, anhydrides, hydroxy groups, and mixtures thereof. Most preferred functional groups (i) are isocyanate groups, alkene groups, and mixtures thereof.

In addition to required functional group (i), material P may optionally comprise one or more additional functional groups (ii), different from required functional group (i). In general, optional functional group (ii) may be defined as any reactive functional group that is reactive with a reactive functional group of a curing agent (B). Illustrative examples include all of those reactive functional groups discussed above in regards to functional group Z and functional group (i).

Examples of suitable oligomers and/or polymers useful as material P include the following: acrylic, modified acrylic, polyurethane, polyester, polylactones, polyurea, alkyd, polysiloxane, polyethers, epoxy upgrades, mixtures thereof, and the like. Oligomers and polymers preferred for use as material P are polyurethane, polyester, acrylic, and the like. Most preferred polymers and oligomers for use as material P are polyurethanes, especially isocyanate functional polyurethane polymers or oligomers.

In one embodiment of the invention, the material P may be an acrylic. The acrylic polymer preferably has a molecular weight of 1000 to 1,000,000, and more preferably of 1500 to 50,000. As used herein, "molecular weight" refers to number average molecular weight, which may be determined by the GPC method using a polystyrene standard. Such polymers are well-known in the art, and can be prepared from monomers such as methyl acrylate, acrylic acid, methacrylic acid, methyl methacrylate, butyl methacrylate, cyclohexyl methacrylate, styrene, maleic anhydride, and the like. The required functional group (i), e.g., isocyanate, or epoxy, cyclic carbonate, anhydride can be incorporated into the ester portion of the acrylic monomer. For example, isocyanate functional acrylic monomers that can be used to form such polymers include isocyanato ethyl methacrylate, glycidyl methacrylate, (2-oxo-1,3-dioxolan-4-yl)methyl methacrylate, and the like. Other acrylic monomers having functional groups (i) in the ester portion of the monomer are also within the skill of the art.

Modified acrylics having the required functional groups (i) can also be used as the material P according to the invention. Such acrylics may be polyester-modified acrylics or polyurethane-modified acrylics, as is well known in the art. Polyester-modified acrylics modified with ε-caprolactone are described in U.S. Pat. No. 4,546,046 of Etzell et al, the disclosure of which is incorporated herein by reference. Polyurethane-modified acrylics are also well known in the art. They are described, for example, in U.S. Pat. No. 4,584,354, the disclosure of which is incorporated herein by reference. A non-limiting example of one such polymer is an acrylic resin made up of hydroxyethyl methacrylate, methyl methacrylate, and butyl acrylate which is then half capped with a diisocyanate such as isophorone diisocyanate to make an isocyanate functional polymer useful as material P.

Polyesters and ester oligomers having functional groups (i) such as isocyanate, or epoxy, cyclic carbonate, anhydride can also be used as the material P in the method of the invention. Such polyesters are well-known in the art, and may be prepared by the polyesterification of organic polycarboxylic acids (e.g., phthalic acid, hexahydrophthalic acid, adipic acid, maleic acid) or their anhydrides with organic polyols containing primary or secondary hydroxyl groups (e.g., ethylene glycol, butylene glycol, 1,6-hexanediol, neopentyl glycol).

The polyesters, formed as described above, will generally have either hydroxy, acid or a mixture of both functionalities. These functionalities (i) can be used for a condensation reaction with monomeric reactive compound (2), or they can be converted into other functionalities that may then react with monomeric reactive compound (2). For example, hydroxy functional polyester may be reacted with a diisocyanate to form an isocyanate functional polyester. The reaction of this material with glycidol will form an epoxy functional polyester with internal urethane links with can then be reacted with monomeric reactive compound (2).

Other functional polyesters can be formed though the use of specialty capping alcohols and acids that are added during the polyester formation. For example, the addition of a hydroxy alkene followed by reaction with hydrogen peroxide will result in the placement of an epoxy group on the polyester. Reaction of this epoxy polyester with carbon dioxide will result in the formation of a cyclic carbonate polyester. In a likewise manner as described above, acid or hydroxy functional ester oligomers can be converted into ester oligomers possessing groups reactable with the functional group Z of monomeric reactive compound (2).

Polyurethanes and urethane oligomers having required functional groups (i) are also known in the art. They can be prepared by a chain extension reaction of a polyisocyanate (e.g., hexamethylene diisocyanate, isophorone diisocyanate, MDI, etc.) and a polyol (e.g., 1,6-hexanediol, 1,4-butanediol, neopentyl glycol, trimethylol propane). Formulating with an appropriate amount of excess polyisocyanate will result in the polyurethane having free isocyanate functionality. Use of glycidol or 3-hydroxypropylene carbonate, for example, will functionalize the polyurethane with epoxy or cyclic carbonate groups respectively. As described above, epoxy and cyclic carbonate groups can be introduced by the capping of the live isocyanate group with a hydroxy alkene, followed by additional reactions as described above.

One class of preferred materials P are those having an internal isocyanurate ring. For example, the isocyanurates of diisocyanates such as isophorone diisocyanate (IPDI) and hexamethylene diisocyanate (HDI) are preferred. In particular, the trimer of IPDI is a most preferred material P. In this case, the required functional groups (i) are the terminal or end-capping isocyanate (homopolymer) groups. While the pure isocyanurates of diisocyanates are preferred, it should be recognized that most commercial sources of isocyanurates also contain additional homopolymers of the diisocyanate and are suitable for use herein.

Illustrative compounds suitable for use as material P include mono or polyfunctional compounds such as non-chain extended aliphatics, cycloaliphatics, aromatics which may or may not contain heteroatoms and which contain a suitable functional group (i) as discussed above.

Examples of compounds suitable for use as material P include simple aliphatic functional materials such as monomeric non-chain extended diisocyanates like hexane diisocyanate, polyamines such as 1,6-hexane diamine, anhydrides such as succinic anhydrides, polyacids such as dodecane dioic acid, compounds having mixed functionality such as hydroxy pivalic acid, the like, and mixtures thereof.

Aromatic functional materials may also be used such as 2,2-bis(4-hydroxyphenyl)propane. Suitable heteroatom functional materials include hydroxyneopentyl hydroxy pivalate. Illustratiave examples of suitable heterocyclic materials include tris-hydroxyethyl isocyanurate, tris-glycidyl isocyanurate, tris(carboxyethyl)isocyanurate, the cyclic carbonate of tris-glycidyl isocyanurate, triamino triazine. Illustrative examples of alkene functional compounds include methyl acrylic acid and its anhydride, glycidyl methacrylate, hydroxy butyl acrylate, 2-oxo-1,3-dioxolan-4-yl)methyl methacrylate, isocyanato ethyl acrylate, and maleic anhydride.

It will further be appreciated that in some instances, monomeric reactive compound (2) may be used as material P so long as it comprises a functional group (i) reactive with a functional group Z. An example of such an instance is when functional group (i) is an ethylenically unsaturated group of a monomer and functional group Z is the ethylenically unsaturated group-containing derivative of a hydroxy group. In this case, the resulting primary carbamate functional material of the invention will be a primary carbamate functional acrylic polymer produced by free radical polymerization.

The material P and monomeric reactive compound (2) are reacted together in the method of the invention to make the primary carbamate functional materials of the invention. In general, the reaction conditions suitable for use herein will be known and recognized to those of ordinary skill in the art. Not withstanding this, it should be appreciated that it is an advantage of the method of the invention that the monomeric reactive compound (2) can be subjected to harsher reaction conditions than may be used with monocarbamate functional reactive compounds of the prior art. For example, reaction temperatures of greater than 140° C. may be used without any appreciable decomposition of monomeric reactive compound (2) occuring. In addition, the monomeric reactive compound (2) used in the method of the invention may be subjected to strong acid or basic reaction conditions. In a most preferred embodiment, the method of the invention will utilize the monomeric reactive compound (2) produced by the method of making compound (2) disclosed above. It is a particular advantage and aspect of this method of making the primary carbamate functional materials of the invention that in substantially all structures resulting there from, substantially all primary carbamate groups X are attached to carbon atoms having a lower degree of substitution than a carbon atom to which linking group L is attached, as discussed below.

The primary carbamate functional materials of the invention will comprise one or more structures be of the formula:

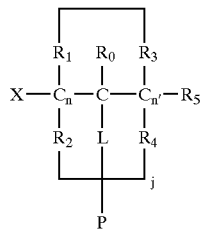

wherein X is a primary carbamate group, n is an integer of 2 or more, n' is an integer of 1 or more, $R_0$, $R_1$, $R_2$, $R_3$, $R_4$ and $R_5$ are independently H, an alkyl group, an aromatic group, or mixtures thereof, at least one $R_1$ or $R_2$ group is not hydrogen, L is a linking group, j is a number equal to 1 or greater, and P is a material selected from the group consisting of a compound, an oligomer, a polymer, and mixtures thereof. It is a requirement of the invention that substantially all primary carbamate groups X are attached to carbon atoms having a lower degree of substitution than a carbon atom to which linking group L is attached.

It will be appreciated that X, n, n', $R_0$, $R_1$, $R_2$, $R_3$, $R_4$, $R_5$, and P are as defined above.

j may be a number equal to one or greater than 1. In a preferred embodiment, j will be between 2 and 50. Most preferably, j will be between 2 and 10. It will thus be appreciated that the primary carbamate functional materials of the invention will be polyfunctional with respect to the primary carbamate functionality.

L is a polyvalent linking group comprising the reaction residue from the reaction between material P and monomeric reactive compound (2). It will thus be appreciated that if monomeric reactive compound (2) contained a hydroxy or halide derivative as functional group Z, linking group L may also comprise any reaction residue from the derivatization reactions converting the hydroxy or halide group Y into a hydroxy or halide derivative group Z.

Illustrative examples of polyvalent linking groups L include esters, ethers, urethanes, ureas, silanes, and the like. Preferred linking groups are urethanes, ureas, and esters with urethanes and esters being most preferred as linking group L.

The curable coating compositions of the invention will comprise the primary carbamate functional materials of the invention as a film-forming component. In a preferred embodiment, the curable coating compositions of the invention will comprise primary carbamate functional polymers and/or oligomers as binders (A). In another embodiment, the primary carbamate functional materials of the invention wherein P is a compound may be used as reactive diluents.

The primary carbamate functional materials of the invention may comprise from 1 to 99% by weight based on total NV film-forming component, more preferably from 1 to 70% by weight, and most preferably from 5 to 50% by weight, based on total NV film-forming component.

The curable coating compositions of the invention may also comprise additional binders (A) comprising one or more active hydrogen-containing groups or groups suitable for UV or free radical cure, a curing agent (B) having one or more functional groups that are reactive with the primary carbamate functional polymers and/or oligomers of the invention or other binders (A)

Examples of suitable additional binders or polymer resins (A) having active hydrogen-containing functional groups on polymer resins are well known in the art. Such groups include, for example, hydroxyl groups, amino groups, thiol groups, hydrazide groups, activated methylene groups, and mixtures thereof. Hydroxyl groups, and mixtures thereof are most preferred hydrogen-containing functional groups.

Suitable polymer resins include, for example, acrylic polymers, modified acrylic polymers, polyesters, polyepoxides, polycarbonates, polyurethanes, polyamides, polyimides, and polysiloxanes, all of which are well known in the art. Preferably, the polymer is an acrylic, modified acrylic or polyester. More preferably, the polymer is an acrylic polymer.

In one preferred embodiment of the invention, the polymer is an acrylic. The acrylic polymer preferably has a molecular weight of 500 to 1,000,000, and more preferably of 1500 to 50,000. As used herein, "molecular weight" refers to number average molecular weight, which may be determined by the GPC method using a polystyrene standard.

Acrylic polymers are well-known in the art, and can be prepared from monomers such as methyl acrylate, acrylic acid, methacrylic acid, methyl methacrylate, butyl methacrylate, cyclohexyl methacrylate, and the like. The active hydrogen-containing functional group can be incorporated into the ester portion of the acrylic monomer through the selection of a suitable ethylenically unsaturated functional monomer. For example, hydroxy-functional acrylic monomers that can be used to form such polymers include hydroxyethyl acrylate, hydroxybutyl acrylate, hydroxybutyl methacrylate, hydroxypropyl acrylate, and the like. Amino-functional acrylic monomers would include t-butylaminoethyl methacrylate and t-butylaminoethylacrylate. Other acrylic monomers having active hydrogen functional groups in the ester portion of the monomer are also within the skill of the art.

Modified acrylics can also be used as the polymer or binder (A) in the curable coating compositions of the invention. Such acrylics may be polyester-modified acrylics or polyurethane-modified acrylics, as is well known in the art. Polyester-modified acrylics modified with ε-caprolactone are described in U.S. Pat. No. 4,546,046 of Etzell et al, the disclosure of which is incorporated herein by reference. Polyurethane-modified acrylics are also well known in the art. They are described, for example, in U.S. Pat. No. 4,584,354, the disclosure of which is incorporated herein by reference.

Polyesters having active hydrogen groups such as hydroxyl groups can also be used as the binder (A) in the curable coating composition according to the invention. Such polyesters are well known in the art, and may be prepared by the polyesterification of organic polycarboxylic acids (e.g., phthalic acid, hexahydrophthalic acid, adipic acid, maleic acid) or their anhydrides with organic polyols containing primary or secondary hydroxyl groups (e.g., ethylene glycol, butylene glycol, neopentyl glycol).

Polyurethanes having active hydrogen functional groups are also well known in the art. They are prepared by a chain extension reaction of a polyisocyanate (e.g., hexamethylene diisocyanate, isophorone diisocyanate, MDI, etc.) and a polyol (e.g., 1,6-hexanediol, 1,4-butanediol, neopentyl glycol, trimethylol propane). They can be provided with active hydrogen functional groups by capping the polyurethane chain with an excess of diol, polyamine, amino alcohol, or the like.

The curable coating compositions of the invention will most preferably include one or more curing agents (B). The primary carbamate functional polymers of the invention and any optional binders (A) are cured via reaction with a component (B) having a plurality of functional groups that are reactive with the primary carbamate groups of the materials of the invention and any reactive functional groups on binder (A). Such reactive groups include active methylol or methylalkoxy groups on aminoplast crosslinking agents or on other compounds such as phenol/formaldehyde adducts, isocyanate groups, siloxane groups, cyclic carbonate groups, and anhydride groups.

Examples of compounds suitable for use as curing agent (B) include melamine formaldehyde resin (including monomeric or polymeric melamine resin and partially or fully alkylated melamine resin), blocked or unblocked polyisocyanates (e.g., TDI, MDI, isophorone diisocyanate, hexamethylene diisocyanate, and isocyanurate trimers of these, which may be blocked for example with alcohols or oximes), urea resins (e.g., methylol ureas such as urea formaldehyde resin, alkoxy ureas such as butylated urea formaldehyde resin), polyanhydrides (e.g., polysuccinic anhydride), and polysiloxanes (e.g., trimethoxy siloxane). Aminoplast resin such as melamine formaldehyde resin or urea formaldehyde resin are especially preferred.

A solvent may optionally be utilized in the curable coating compositions of the present invention. Although the composition used according to the present invention may be utilized, for example, in the form of substantially solid powder, or a dispersion, it is often desirable that the composition is in a substantially liquid state, which can be accomplished with the use of a solvent. This solvent should act as a solvent with respect to all polymeric and/or oligomeric components. In general, depending on the solubility characteristics of the polymeric components, the solvent can be any organic solvent and/or water. In one preferred embodiment, the solvent is a polar organic solvent. More preferably, the solvent is a polar aliphatic solvents or polar aromatic solvents. Still more preferably, the solvent is a ketone, ester, acetate, aprotic amide, aprotic sulfoxide, or aprotic amine. Examples of useful solvents include methyl ethyl ketone, methyl isobutyl ketone, m-amyl acetate, ethylene glycol butyl ether-acetate, propylene glycol monomethyl ether acetate, xylene, N-methylpyrrolidone, or blends of aromatic hydrocarbons. In another preferred embodiment, the solvent is water or a mixture of water with small amounts of co-solvents.

Depending on the make up of the rest of the paint composition, it is also possible to have a liquid paint that has low levels of additional solvents wherein unreacted monomeric reactive compound (2) is left the primary carbamate functional reaction product mixture to function as a reactive diluent. In a most preferred case, no solvent other than excess monomeric reactive compound (2) will be present. It will be appreciated that this provides an essentially zero VOC coating since the compound (2) will ultimately enter into the film-forming reaction.

The curable coating compositions of the invention may include a catalyst to enhance the cure reaction. For example, when aminoplast compounds, especially monomeric melamines, are used as curing agent (B), a strong acid catalyst may be utilized to enhance the cure reaction. Such catalysts are well known in the art and include, for example, p-toluenesulfonic acid, dinonylnaphthalene disulfonic acid, dodecylbenzenesulfonic acid, phenyl acid phosphate, monobutyl maleate, butyl phosphate, and hydroxy phosphate ester. Strong acid catalysts are often blocked, e.g. with an amine. Other catalysts that may be useful in the composition of the invention include Lewis acids, zinc salts, and tin salts.

In a preferred embodiment of the invention, the solvent is present in the coating composition in an amount of from about 0.01 weight percent to about 99 weight percent, preferably from about 10 weight percent to about 60 weight percent, and more preferably from about 30 weight percent to about 50 weight percent.

Any additional agent used, for example, surfactants, fillers, stabilizers, wetting agents, dispersing agents, adhesion promoters, UV absorbers, HALS, etc. may be incorporated into the coating composition of the invention. While the agents are well-known in the prior art, the amount used must be controlled to avoid adversely affecting the coating characteristics.

The curable coating compositions of the invention may be used in a wide variety of applications, such as primers, basecoats, clearcoats, two-component systems, anti-chip coating compositions, water borne coatings, solvent borne coatings, coatings for flexible substrates, solventless coatings, powder coatings, and the like. In a preferred embodiment, the curable coating compositions of the invention are preferably utilized in a high-gloss coating and/or as the clearcoat of a composite color-plus-clear coating. High-gloss coatings as used herein are coatings having a 20° gloss (ASTM D523-89) or a DOI (ASTM E430-91) of at least 80.

When the coating composition of the invention is used as a high-gloss pigmented paint coating, the pigment may be any organic or inorganic compounds or colored materials, fillers, metallic or other inorganic flake materials such as mica or aluminum flake, and other materials of kind that the art normally names as pigments. Pigments are usually used in the composition in an amount of 1% to 100%, based on the total solid weight of components A, B and C (i.e., a P:B ratio of 0.1 to 1).

When the coating composition according to the invention is used as the clearcoat of a composite color-plus-clear coating, the pigmented basecoat composition may any of a number of types well known in the art, and does not require explanation in detail herein. Polymers known in the art to be useful in basecoat compositions include acrylics, vinyls, polyurethanes, polycarbonates, polyesters, alkyds, and polysiloxanes. Preferred polymers include acrylics and polyurethanes. In one preferred embodiment of the invention, the basecoat composition also utilizes a carbamate-functional acrylic polymer. Basecoat polymers may be thermoplastic, but are preferably crosslinkable and comprise one or more type of cross-linkable functional groups. Such groups include, for example, hydroxy, isocyanate, amine, epoxy, acrylate, vinyl, silane, and acetoacetate groups. These groups may be masked or blocked in such a way so that they are unblocked and available for the cross-linking reaction under the desired curing conditions, generally elevated temperatures. Useful cross-linkable functional groups include hydroxy, epoxy, acid, anhydride, silane, and acetoacetate groups. Preferred cross-linkable functional groups include hydroxy functional groups and amino functional groups.

Basecoat polymers may be thermoplastic, self-crosslinkable, or may require a separate cross-linking agent that is reactive with the functional groups of the polymer. When the polymer comprises hydroxy functional groups, for example, the cross-linking agent may be an aminoplast resin, isocyanate and blocked isocyanates (including isocyanurates), and acid or anhydride functional cross-linking agents.

Coating compositions of the invention can be coated on an article or surface by any of a number of techniques well known in the art. These include, for example, spray coating, dip coating, roll coating, curtain coating, and the like. For automotive body panels, spray coating is preferred.

The coating compositions described herein are preferably subjected to conditions so as to cure the coating layers. Although various methods of curing may be used, heat-curing is preferred. Generally, heat curing is effected by exposing the coated article to elevated temperatures provided primarily by radiative heat sources. Curing temperatures will vary depending on the particular blocking groups used in the cross-linking agents, however they generally range between 93° C. and 177° C. The compounds (C) according to the present invention are reactive even at relatively low cure temperatures. Thus, in a preferred embodiment, the cure temperature is preferably between 115° C. and 150° C., and more preferably at temperatures between 115° C. and 138° C. for a blocked acid catalyzed system. For an unblocked acid catalyzed system, the cure temperature is preferably between 82° C. and 99° C. The curing time will vary depending on the particular components used, and physical parameters such as the thickness of the layers, however, typical curing times range from 15 to 60 minutes, and preferably 15–25 minutes for blocked acid catalyzed systems and 10–20 minutes for unblocked acid catalyzed systems.

The invention is further described in the following examples. All parts and percentages are by weight unless otherwise specified.

EXAMPLES

Example 1a

Preparation of a Monomeric Reactive Compound (2)

A mixture of 55.69 parts of 2-ethyl-1,3-hexanediol, 20.94 parts of methyl carbamate, 23.26 parts of toluene and 0.07 parts of dibutyl tin oxide were heated under an inert atmosphere to reflux in a reactor equipped with an extractor that can remove methanol but returns toluene to the reaction mixture. Once at reflux, the inert atmosphere was turned off. An additional 0.04 parts of dibutyl tin oxide was added after the first three hours at reflux. Additional toluene was added to the reaction mixture to keep the reflux temperature below 130° C. The reaction was stopped when ~85% of the theoretical amount of hydroxy groups were converted into carbamate groups. Free methyl carbamate, toluene and some of the unconverted 2-ethyl-1,3-hexanediol was then removed by vacuum distillation. The final product was a mixture of 55.5% 2-ethyl-1,3-hexanediol, 42.3% 3-hydroxy-2-ethyl carbamate and 2.2% 2-ethylhexane1,3-dicarbamate.

Example 1b

Preparation of the Monomeric Reactive Compound (2)

A mixture of 45.52 parts of 2-ethyl-1,3-hexanediol, 23.4 parts of methyl carbamate, 0.08 parts butyltin hydroxide oxide and 30.4 parts toluene was headed heated under an inert atmosphere to reflux in a reactor equipped with an extractor that can remove methanol but return toluene to the reaction mixture. Once at reflux, the inert atmosphere was turned off. The reaction was stopped when approximately half of the theoretical amount of mono-carbamate product was formed. Then 0.6 parts of octanethiol was added and the reaction mixture was held at 100° C. for 1.5 hours. Free methyl carbamate, toluene, octanethiol and some of the unconverted 2-ethyl-1,3-hexanediol was then removed by vacuum distillation. The final product was a mixture of 43.0% 2-ethyl-1,3-hexanediol and 53.2% 3-hydroxy-2-ethylhexane carbamate and 3.7% 2-ethyl-1,3-hexane dicarbamate.

Example 2a

Preparation of a Carbamate Functional Oligomers According to the Invention

A mixture of 30 parts of anhydrous methyl ethyl ketone and 23.2 parts of hexane diisocyanate were heated under an inert atmosphere to 60° C. Then 0.05 parts of dibutyl tin dilaurate was added. Then 31.8 parts of the monomeric reactive compound (2) from Example 1a was added slowly to the reaction mixture. Once the addition was complete, 4.5 parts of methyl ethyl ketone was added and the reaction mixture heated to 75° C. and kept there until the reaction mixture was free of isocyanurate. The methyl ethyl ketone was then removed by vacuum distillation and 10.35 parts of propylene glycol monopropyl ether added. The final oligomer had a NV of 82.3% and a carbamate equivalent weight of 532 g/equ.

Example 2b

Preparation of a Carbamate Functional Oligomer According to the Invention

A mixture of 28.17 parts of material from example 1b, 3.50 parts 2-ethyl-1,3-hexanediol and 21.38 parts propylene glycol methyl ether acetate was heated to 60° C. under an inert atmosphere in a reactor equipped with a condensation apparatus. Once at 60° C., 0.016 parts dibutyltin dilaurate was added, and then followed with incremental additions of 20.06 parts hexamethylene diisocyanate. The solution was held at 80° C. until the isocyanate functionality was consumed. Subsequently, 4.34 parts of hydroxy propyl carbamate, and 0.030 parts dibutyltin dilaurate was added to the solution while allowing it to cool down to 65° C. Once the solution reached 65° C., 12.98 parts of the isocyanurate form of isophorone diisocyanate was added. The mixture was then heated to 80° C. and allowed to proceed to completion. The resultant product was then reduced with 0.81 parts of iso-butanol and 8.72 parts propylene glycol methyl ether acetate.

Example 3

Preparation and Evaluation of the Curable Coating Compositions of the Invention and Curable Coating Compositions of the Prior Art The following materials where added in order to a stainless steel one-quart container and subsequently placed under medium agitation (a mixing blade) for approximately fifteen to twenty minutes.

The samples were evaluated as follows for weathering (WOM Exposure E27699), adhesion (GM-9071PA), scratch and mar (LP-463PB-54-01), and Jacksonville etch.

All test panels were D&D 161B grey TPO (Solvay) which had been acid washed followed a basic wash. Test panels except for etch panels were treated with an adhesion promoter U04KM039C, commercially available from BASF Corporation. Clearcoat samples C-I, C-II, A, and B were spray applied wet on wet over solvent borne black acrylic/melamine based basecoat, commercially available from BASF Corporation as E98KM405. Clearcoat samples C-III, C-IV, C-V, C, D, and E for Jacksonville etch were spray applied wet on wet over solvent borne black acrylic/melamine based basecoat, commercially available from BASF Corporation as E86KM524U. The basecoat was flashed 5 minutes at ambient. The resulting composite color plus clear compositions for clearcoat samples C-I, C-II, A, and B were cured for 30 minutes at 265° F., while those for clearcoat samples C-III, C-IV, C-V, C, D, and E were cured 30 minutes at 250° F. Clearcoat film builds were 1.6 to 1.8 mils, basecoat film builds 0.6 to 0.9 mils.

WOM exposure was evaluated using a WOM E27699 as follows. % retention was measured on panels 1, 2 and 3. Panel 1 was evaluated at 2759 hours and 3587 Kj. Panel 2 was evaluated at 2759 hours and 3587 Kj plus humidity.

| Component | C-I | A | C-II | B | C-III | C | C-IV | D | C-V | E |
|---|---|---|---|---|---|---|---|---|---|---|
| Resin from Ex. 2a | — | 141.58 | — | 100.89 | — | — | — | — | — | — |
| Resin from Ex. 2b | — | — | — | — | — | 312.99 | — | 270.74 | — | 222.22 |
| Carbamate functional resin[1] | 700.87 | — | 499.46 | — | 473.19 | — | 409.31 | — | 335.96 | — |
| Carbamate functional resin[2] | 272.75 | 68.19 | 545.54 | 136.38 | 0.00 | 0.00 | 81 | 54.00 | 174.00 | 116.00 |
| Curing Agent[3] | 331.70 | 88.01 | 367.87 | 95.59 | 167.86 | 103.67 | 176.17 | 110.32 | 185.70 | 117.95 |
| Catalyst[4] | 28.75 | 7.35 | 29.87 | 7.58 | 14.44 | 9.37 | 14.70 | 9.58 | 14.99 | 9.81 |
| UVA | 28.75 | 7.35 | 29.87 | 7.58 | 14.44 | 9.37 | 14.70 | 9.58 | 14.99 | 9.81 |
| HALS | 5.75 | 1.47 | 5.97 | 1.52 | 2.89 | 1.87 | 2.94 | 1.92 | 3.00 | 1.96 |
| Flow Additive[5] | 7.99 | 2.04 | 8.30 | 2.11 | 4.01 | 2.60 | 4.08 | 2.66 | 4.16 | 2.73 |
| Rheology Control Agent[6] | 99.79 | 25.49 | 103.67 | 26.30 | 50.11 | 32.53 | 51.00 | 33.24 | 52.02 | 34.06 |
| n-butyl acetate | 200.01 | 86.77 | 150.91 | 63.93 | 163.00 | 105.22 | 151.85 | 103.76 | 139.05 | 90.25 |
| n-butanol | 143.77 | 36.73 | 149.35 | 37.90 | 24.07 | 15.62 | 24.49 | 10.45 | 24.98 | 16.35 |
| % NV | 57 | 57 | 57 | 57 | 57 | 57 | 57 | 57 | 57 | 57 |

[1] 65% NV carbamate functional resin per U.S. Pat. No. 6,423,788.
[2] 50% NV Carbamate functional resin per the examples of U.S. Pat. No. 5,512,639
[3] Fully alkylated (50/50 methyl/butyl) monomeric aminoplast
[4] 25% blocked DDBSA in methanol
[5] polysiloxane flow additive
[6] 9.6% fumed silica ground in a 65% NV carbamate functional acrylic resin per U.S. Pat. No. 5,552,497

Panel 3 was evaluated at 4413 hours and 5737 Kj.

| Sample | Panel 1 | Panel 2 | X cut Adhesion | Panel 3 |
|---|---|---|---|---|
| C-I | 104.49 | 102.25 | P | 87.64 |
| A | 103.33 | 100.00 | P | 97.78 |
| C-II | 103.33 | 101.11 | P | 91.01 |
| B | 103.33 | 102.22 | P | 93.33 |

It can be seen the curable coating compositions of the invention showed significant improvement over prior art coating compositions in panel 3.

Adhesion, scratch & mar and environmental etch resistance were evaluated after CAR-045 Puerto Rico exposure testing as follows. The higher the % retention the better the performance in scratch and mar. The visual rating for scratch & mar and etch is as follows: 1=excellent, 2=very good, 3=good, 4=poor, 5=very poor.

| | Adhesion (GM-9071P A) | | | Scratch & Mar LP-463PB-54-01 | 14 wk Etch |
|---|---|---|---|---|---|
| Sample | Panel 1 | Panel 2 | Panel 3 | % retention Visual | Visual |
| C-I | P | P | P | 80    5 | 5 |
| A | P | P | P | 100   1 | 4 |
| C-II | P | P | P | 82    5 | 5 |
| B | P | P | P | 88    2 | 4 |

It can be seen that the curable coating compositions of the invention showed significant improvement over the prior art in scratch & mar and environmental etch resistance.

The environmental etch resistance of samples C-III, C-IV, C-V, C, D, and E was evaluated in Jacksonville, Fla. testing as follows. In this case, a rating of 7 or better was a pass with anything less than a 7 being a failure. The smaller the rating, the better the etch resistance.

| Sample | Etch rating |
|---|---|
| C-III | 9 |
| C | 6 |
| C-IV | 10A |
| D | 5 |
| C-V | 10 |
| E | 5 |

It can be seen that the curable coating compositions of the invention showed significant improvement over the prior art in environmental etch resistance as tested in Jacksonville, Fla. testing.

What is claimed is:

1. A primary carbamate functional material of the formula:

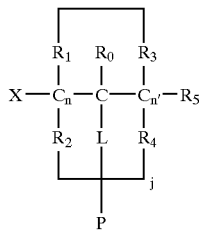

wherein

X is a primary carbamate group, n is an integer of 2 or more, n' is an integer of 1 or more, $R_0$, $R_1$, $R_2$, $R_3$, $R_4$ and $R_5$ are independently H, an alkyl group, an aromatic group, or mixtures thereof, at least one $R_1$ or $R_2$ group is not hydrogen, L is a linking group, j is a number equal to 1 or greater, P is a material selected from the group consisting of a compound, an oligomer, a polymer, and mixtures thereof, substantially all primary carbamate groups X are attached to carbon atoms having a lower degree of substitution than a carbon atom to which linking group L is attached, and the primary carbamate functional material comprises the reaction product of (1) at least one material P comprising one or more functional groups (i) which are reactive with a functional group Z but which are substantially nonreactive with a primary carbamate group X of monomeric reactive compound (2), (2) a monomeric reactive compound comprising one or more structures of the formula:

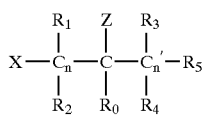

wherein

X is a primary carbamate group,

Z is a functional group reactive with at least one functional group of material (1) and is selected from the group consisting of hydroxy groups, halide groups, and derivatives thereof, n is an integer of 2 or more, n' is an integer of 1 or more, and $R_0$, $R_1$, $R_2$, $R_3$, $R_4$ and $R_5$ are independently H, an alkyl group, an aromatic group, or mixtures thereof, with the provisos that (i) at least one $R_1$ or $R_2$ group is not hydrogen, and (ii) in substantially all structures, primary carbamate group X is attached to a carbon atom having a lower degree of substitution than a carbon atom to which functional group Z is attached.

2. The primary carbamate functional material of claim 1 wherein linking group L is the reaction product of functional group (i) of material P and functional group Z of monomeric reactive compound (2).

3. The primary carbamate functional material of claim 2 wherein linking group L further comprises the reaction product of a reaction converting a hydroxy group into a derivative group of a hydroxy group.

4. The primary carbamate functional material of claim 2 wherein linking group L further comprises the reaction product of a reaction converting a halide group into a derivative group of a halide group.

5. The primary carbamate functional material of claim 2 wherein linking group L is selected from the group consisting of esters, ethers, urethanes, ureas, and silanes.

6. The primary carbamate functional material of claim 5 wherein linking group L is selected from the group consisting of esters and urethanes.

7. The primary carbamate functional material of claim 1 wherein Z is a functional derivative of a hydroxy group or a halide group.

8. The primary carbamate functional material of claim 7 wherein Z is a functional derivative of a hydroxy group or a halide group selected from the group consisting of acid groups, epoxy groups, cyclic carbonate groups, silane groups, isocyanate groups, amine groups especially primary and secondary amines, silicon hydrides, alkenes, organometallics, and mixtures thereof.

9. The primary carbamate functional material of claim 1 wherein j is 1.

10. The primary carbamate functional material of claim 9 wherein j is between 2 and 50.

11. The primary carbamate functional material of claim 10 wherein j is between 2 and 10.

12. The primary carbamate functional material of claim 1 wherein P is a compound.

13. The primary carbamate functional material of claim 12 wherein P is a compound having a number average molecular weigh of from 68 to 2000.

14. The primary carbamate functional material of claim 12 wherein P is a compound selected from the group consisting of mono or polyfunctional compounds.

15. The primary carbamate functional material of claim 14 wherein P is a compound selected from the group consisting of nonchain extended aliphatics, cycloaliphatics, aromatics, polyamines, anhydrides, polyacids, heterocyclic compounds, alkene functional compounds, and mixtures thereof.

16. The primary carbamate functional material of claim 1 wherein P is an oligomer.

17. The primary carbamate functional material of claim 16 wherein j is more than 1.

18. The primary carbamate functional material of claim 17 wherein j is between 2 and 10.

19. The primary carbamate functional material of claim 16 wherein P is an oligomer having from 2 to 9 repeating units.

20. The primary carbamate functional material of claim 16 wherein P is an oligomer having a number average molecular weight in the range of from 200 to 1499 Daltons.

21. The primary carbamate functional material of claim 1 wherein P is a polymer.

22. The primary carbamate functional material of claim 21 wherein j is more than 1.

23. The primary carbamate functional material of claim 22 wherein j is between 2 and 50.

24. The primary carbamate functional material of claim 1 wherein P further comprises one or more additional functional groups (ii) that are substantially nonreactive with primary carbamate group X but which are different from functional group (i).

25. The primary carbamate functional material of claim 1 wherein the monomeric reactive compound (2) is made by a method comprising:
providing a compound (a) having a functional group $F_i$ and a functional group $F_{ii}$ separated by at least three carbon atoms, wherein:
(1.) said functional groups $F_i$ and $F_{ii}$ are each hydroxy or halide groups, and
(2.) functional group $F_i$ is attached to a carbon atom having a lower degree of substitution than a carbon atom to which functional group $F_{ii}$ is attached,
providing one or more compounds (b) having at least one functional group (iii) reactive with functional group $F_i$ to produce a primary carbamate group, and
reacting compound (a) with compound (b) to produce a compound of the formula:

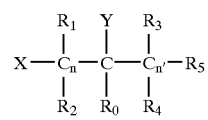

wherein
X is a primary carbamate group,
Y is a hydroxy or halide group,
n is an integer of 2 or more,
n' is an integer of 1 or more, and
$R_0$, $R_1$, $R_2$, $R_3$, $R_4$ and $R_5$ may be independently H or a group selected from aliphatic groups, cycloaliphatic groups, aromatic groups and mixtures thereof,
with the provisos that
(i) at least one of the $R_1$ and $R_2$ groups is not hydrogen, and
(ii) primary carbamate group X is attached to a carbon atom having a lower degree of substitution than a carbon atom to which functional group Y is attached.

26. The carbamate functional material of claim 1 wherein monomeric reactive compound (2) comprises one structure.

27. The carbamate functional material of claim 21 wherein monomeric reactive compound (2) comprises at least two structures.

28. The carbamate functional material of claim 1 wherein monomeric reactive compound (2) comprises at least four structures.

29. The carbamate functional material of claim 1 wherein Z is a hydroxy group.

30. The carbamate functional material of claim 1 wherein n is an integer of from 2 to 12.

31. The carbamate functional material of claim 30 wherein n is an integer of from 2 to 8.

32. The carbamate functional material of claim 31 wherein n is an integer of from 2 to 4.

33. The carbamate functional material of claim 1 wherein n is an integer of at least 3.

34. The carbamate functional material of claim 33 wherein n is an integer of from 3 to 12.

35. The carbamate functional material of claim 34 wherein n is an integer of from 3 to 4.

36. The carbamate functional material of claim 1 wherein n' is an integer of from 1 to 16.

37. The carbamate functional material of claim 36 wherein n' is 1 to 12.

38. The carbamate functional material of claim 37 wherein n' is 1 to 8.

39. The carbamate functional material of claim 1 wherein at least one of the substituents $R_1$ and $R_2$ on the carbon to which X is attached is hydrogen.

40. The carbamate functional material of claim 39 wherein both of the substituents $R_1$ and $R_2$ on the carbon to which X is attached are hydrogen.

41. The carbamate functional material of claim 40 wherein $R_0$ is H.

42. The carbamate functional material of claim 40 wherein $R_0$ is not hydrogen.

43. The carbamate functional material of claim 42 wherein $R_0$ is selected from the group consisting of $C_1$–$C_{16}$ aliphatic groups, $C_1$–$C_{16}$ cycloaliphatic groups, $C_1$–$C_{16}$ aromatic groups, and mixtures thereof.

44. The carbamate functional material of claim 43 wherein $R_0$ is selected from the group consisting of $C_1$–$C_{12}$ aliphatic groups.

45. The carbamate functional material of claim 44 wherein $R_0$ is selected from the group consisting of $C_1$–$C_8$ aliphatic groups.

46. The carbamate functional material of claim 39 wherein at least one of the substituents $R_1$ and $R_2$ on the carbon to which X is attached is not hydrogen and $R_0$ is not hydrogen.

47. The carbamate functional material of claim 46 wherein at least one of the $R_1$ or $R_2$ groups on the carbon to which X is attached is selected from the group consisting of $C_1$–$C_{16}$ aliphatic groups, $C_1$–$C_{16}$ cycloaliphatic groups, $C_1$–$C_{16}$ aromatic groups and mixtures thereof.

48. The carbamate functional material of claim 47 wherein $R_0$ is selected from the group consisting of $C_1$–$C_{16}$ aliphatic groups, $C_1$–$C_{16}$ cycloaliphatic groups, $C_1$–$C_{16}$ aromatic groups, and mixtures thereof.

49. The carbamate functional material of claim 48 wherein $R_0$ is selected from the group consisting of $C_1$–$C_{12}$ aliphatic groups.

50. The carbamate functional material of claim 49 wherein $R_0$ is selected from the group consisting of $C_1$–$C_8$ aliphatic groups.

51. The carbamate functional material of claim 1 wherein the at least one $R_1$ or $R_2$ group that is not hydrogen is attached to a carbon atom located in closer proximity to the carbon atom to which functional group Y is attached than to the carbon atom to which functional group X is attached.

52. The carbamate functional material of claim 51 wherein n is 2 and the at least one $R_1$ or $R_2$ group that is not hydrogen is attached to a carbon atom located an equal distance between the carbon atom to which functional group Y is attached and the carbon atom to which functional group X is attached.

53. The carbamate functional material of claim 51 wherein n is 3 or greater and the at least one $R_1$ or $R_2$ group that is not hydrogen is attached to a carbon atom located in closer proximity to the carbon atom to which functional group Y is attached than to the carbon atom to which functional group X is attached.

54. The carbamate functional material of claim 53 wherein n is 3 or greater and the at least one $R_1$ or $R_2$ group that is not hydrogen is attached to a carbon atom which is adjacent to the carbon atom to which functional group Y is attached.

55. The carbamate functional material of claim 1 wherein $R_3$, $R_4$ and $R_5$ are selected from the group consisting of H, $C_1$–$C_{16}$ aliphatic groups, $C_1$–$C_{16}$ cycloaliphatic groups, $C_1$–$C_{16}$ aromatic groups, and mixtures thereof.

56. The carbamate functional material of claim 1 wherein n' is greater than 1 and at least one of $R_3$, $R_4$ and $R_5$ are selected from the group consisting of $C_1$–$C_{16}$ aliphatic groups, $C_1$–$C_{16}$ cycloaliphatic groups, $C_1$–$C_{16}$ aromatic groups, and mixtures thereof.

57. The carbamate functional material of claim 56 wherein at least two of $R_3$, $R_4$ and $R_5$ are selected from the group consisting of $C_1$–$C_{16}$ aliphatic groups, $C_1$–$C_{16}$ cycloaliphatic groups, $C_1$–$C_{16}$ aromatic groups, and mixtures thereof.

58. The carbamate functional material of claim 57 wherein at least three of $R_3$, $R_4$ and $R_5$ are selected from the group consisting of $C_1$–$C_{16}$ aliphatic groups, $C_1$–$C_{16}$ cycloaliphatic groups, $C_1$–$C_{16}$ aromatic groups, and mixtures thereof.

59. A primary carbamate functional material consisting of the formula:

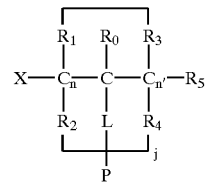

wherein

X is a primary carbamate group, n is an integer of 2 or more, n' is an integer of 1 or more, $R_0$, $R_1$, $R_2$, $R_3$, $R_4$ and $R_5$ are independently H, an alkyl group, an aromatic group, or mixtures thereof, at least one $R_1$ or $R_2$ group is not hydrogen, L is a linking group, j is a number equal to 1 or greater, P is a material selected from the group consisting of a compound, an oligomer, a polymer, and mixtures thereof, primary carbamate group X is attached to a carbon atom having a lower degree of substitution than a carbon atom to which linking group L is attached, and the primary carbamate functional material comprises the reaction product of (1) at least one material selected from the group consisting of a compound, an oligomer, a polymer, and mixtures thereof, said material comprising one or more functional groups which are reactive with a functional group Z but which are substantially nonreactive with a primary carbamate group X of monomeric reactive compound (2), (2) a monomeric reactive compound comprising one or more structures of the formula:

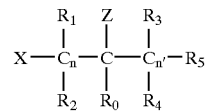

wherein

X is a primary carbamate group,

Z is a functional group reactive with at least one functional group of material (1) and is selected from the group consisting of hydroxy groups, halide groups, and derivatives thereof, n is an integer of 2 or more, n' is an integer of 1 or more, and $R_0$, $R_1$, $R_2$, $R_3$, $R_4$ and $R_5$ are independently H, an alkyl group, an aromatic group, or mixtures thereof, with the provisos that (i) at least one $R_1$ or $R_2$ group is not hydrogen, and (ii) in substantially all structures, primary carbamate group X is attached to a carbon atom having a lower degree of substitution than a carbon atom to which functional group Z is attached.

60. A curable coating composition comprising the primary carbamate functional material of claim 1.

61. The curable coating composition of claim 60 further comprising a curing agent comprising one or more functional groups reactive with the primary carbamate groups X.

62. A method of making a primary carbamate functional material, comprising reacting (1) at least one material P selected from the group consisting of a compound, an oligomer, a polymer, and mixtures thereof, said material comprising one or more functional groups (i) which are reactive with a functional group Z but which are substantially nonreactive with a primary carbamate group X of monomeric reactive compound (2), and (2) a monomeric reactive compound comprising one or more structures of the formula:

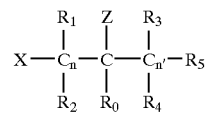

wherein

X is a primary carbamate group,

Z is a functional group reactive with at least one functional group of material (1) and is selected from the group consisting of hydroxy groups, halide groups, and derivatives thereof, n is an integer of 2 or more, n' is an integer of 1 or more, and $R_0$, $R_1$, $R_2$, $R_3$, $R_4$ and $R_5$ are independently H, an alkyl group, an aromatic group, or mixtures thereof, with the provisos that (i) at least one $R_1$ or $R_2$ group is not hydrogen, and (ii) in substantially all structures, primary carbamate group X is attached to a carbon atom having a lower degree of substitution than a carbon atom to which functional group Z is attached.

* * * * *